(12) United States Patent
Dennis et al.

(10) Patent No.: US 7,745,489 B2
(45) Date of Patent: Jun. 29, 2010

(54) COMPOSITIONS AND METHODS FOR INHIBITION OF PHOSPHOLIPASE A2 MEDIATED INFLAMMATION

(75) Inventors: Edward Dennis, La Jolla, CA (US); Tony Yaksh, San Diego, CA (US); Karin Killermann Lucas, San Diego, CA (US); Camilla Svensson, San Diego, CA (US); David A. Six, Durham, NC (US); George Kokotos, Athens (GR); Violetta Constantinou-Kokotou, Athens (GR)

(73) Assignee: The Regents of the University of California, Oakland, CA (US)

( * ) Notice: Subject to any disclaimer, the term of this patent is extended or adjusted under 35 U.S.C. 154(b) by 1502 days.

(21) Appl. No.: 10/506,059

(22) PCT Filed: Mar. 7, 2003

(86) PCT No.: PCT/US03/07076

§ 371 (c)(1),
(2), (4) Date: Feb. 18, 2005

(87) PCT Pub. No.: WO03/076389

PCT Pub. Date: Sep. 18, 2003

(65) Prior Publication Data

US 2005/0148549 A1  Jul. 7, 2005

Related U.S. Application Data

(60) Provisional application No. 60/362,701, filed on Mar. 7, 2002.

(51) Int. Cl.
- A61K 31/185  (2006.01)
- A61K 31/195  (2006.01)
- C07F 9/28  (2006.01)
- C07C 229/00  (2006.01)
- C07C 205/00  (2006.01)

(52) U.S. Cl. .......... 514/553; 514/563; 562/15; 562/450; 562/553

(58) Field of Classification Search ............... 560/155; 562/567, 15, 450, 553; 514/183, 400, 553, 514/563

See application file for complete search history.

(56) References Cited

U.S. PATENT DOCUMENTS 5,089,492 A * 2/1992 Gerling et al. ............... 514/183
5,889,040 A * 3/1999 Beale et al. .................. 514/400

FOREIGN PATENT DOCUMENTS

JP  48004421  * 5/1971

* cited by examiner

Primary Examiner—Taylor Victor Oh
(74) Attorney, Agent, or Firm—DLA Piper LLP (US)

(57) ABSTRACT

Specific, highly potent 2-oxo-amide based inhibitors of phospholipase $A_2$ ($PLA_2$) activity are provided. A role for $PLA_2$ activity in spinally mediated inflammatory processes is established, and a method for treating hyperalgesia and other inflammatory conditions associated with $PLA_2$ activity is provided.

12 Claims, 15 Drawing Sheets

A.

COMPOSITIONS AND METHODS FOR INHIBITION OF PHOSPHOLIPASE A2 MEDIATED INFLAMMATION

CROSS-REFERENCE TO RELATED PATENT APPLICATIONS

This application claims the priority of U.S. Provisional Patent Application No. 60/362,701, filed on Mar. 7, 2002.

GRANT INFORMATION

This invention was made in part with government support under the National Institutes of Health (NIH Grant GM20508). The United States Government has certain rights in this invention.

FIELD OF THE INVENTION

The present invention relates generally to the field of non-steroidal anti-inflammatory agents for inhibition of phospholipase A2 enzymes, and the use of such agents in controlling inflammation.

BACKGROUND OF THE INVENTION

Injury to one part of the body often results in hypersensitivity to painful stimuli. It has recently been discovered that this phenomenon is not, as previously thought, driven only by transmission of nerve impulses from a site of peripheral inflammation through the spinal cord to the brain. Rather, Samad, et al. have opined that hyperalgesia results from facilitation of pain processing signals inside the brain and spinal cord. Samad, et al., *Nature* 410, 471-475 (2001).

One theory as to how such signalling occurs posits that an increase in cerebrospinal levels of interleukin-1β may signal the central nervous system that an injury to the body has occurred. Eck, et al. have suggested that interleukin-1β may interact with cells at the blood-brain barrier to stimulate expression of cyclooxygenase-2 and prostaglandin E synthase. Eck, *Nature* 410: 430-431 (2001).

Following hydrolysis of arachidonic acid from phospholipid by phospholipase $A_2$, cyclooxygenase-2 converts arachidonic acid into prostaglandin $H_2$. In turn, prostaglandin E synthase converts prostaglandin $H_2$ into prostaglandin $E_2$, a potent inflammatory mediator. Prostaglandin $E_2$ also activates the synthesis of interleukin-1β by microglia (possibly explaining the latter's presence in cerebrospinal fluid).

Whatever the specific mechanism, the end product of the central cyclooxygenase signaling cascade is enhanced pain and inflammation.

To date, therapeutic proposals to target the cyclooxygenase signalling cascade to treat hyperalgesia have focused on inhibition of cyclooxygenase-2 activity. See, e.g., Bartfai, T., *Nature* 410: 425-427 (2001); referencing Samad, et al. and Eck, supra. However, current pain remedies and anti-inflammatories commonly employed to this end are either potentially addictive opiates or are non-steroidal anti-inflammatories (NSAIDS) designed to target the cyclooxygenase enzymes (e.g., aspirin, ibuprofen, ketorolac, Celebrex™ and Vioxx™). Cyclooxygenase-2 is also the target of most antipyretic (fever-reducing) drugs.

Phospholipase $A_2$ ($PLA_2$) has not received much attention as a therapeutic target in the cyclooxygenase signaling cascade. To the contrary, it has been reported that no increase in $PLA_2$ activity in the spinal cord or brain is produced in response to peripheral injury in an animal model (rat paw edema). See, e.g., Samad, et al., at 471 and 473, FIG. 2, which recently concluded that "COX-2 [cyclooxygenase-2] alone appears to be pivotal in central [nervous system] $PGE_2$ induction." Id., at 471.

SUMMARY OF THE INVENTION

The invention provides potent inhibitors of phospholipase $A_2$ ($PLA_2$), and methods for use of the inhibitory compounds. In the latter respect, it has been discovered that $PLA_2$ is both present and active in the spinal cord. In particular, it is causatively related to spinally mediated inflammatory processes, suggesting a new method for treating inflammation, pain, hyperalgesia (pain experienced through hypersensitivity to stimulus), and other conditions causatively related to inflammation (e.g., neurological disorders stemming from inflammation affecting the central nervous system (CNS)). The inhibitory compounds of the invention are especially useful in treating these conditions, and act on $PLA_2$ rather than on the cyclooxygenase enzymes.

The $PLA_2$ inhibitors of the invention are 2-oxoamide compounds, including compounds which exhibit a high degree of specificity for particular isoforms of $PLA_2$, such as the cytosolic ($cPLA_2$) and calcium-independent ($iPLA_2$) isoforms of the molecule, one or both of which are present in many different cell types. At dosages well below cytotoxic levels, the $PLA_2$ inhibitors can completely abrogate prostaglandin production (induced, in experimental models, by LPS). Thus, the $PLA_2$ inhibitors of the invention are especially useful agents for treating inflammation, pain and hyperalgesia.

DETAILED DESCRIPTION OF THE PREFERRED EMBODIMENTS

Figure 1:
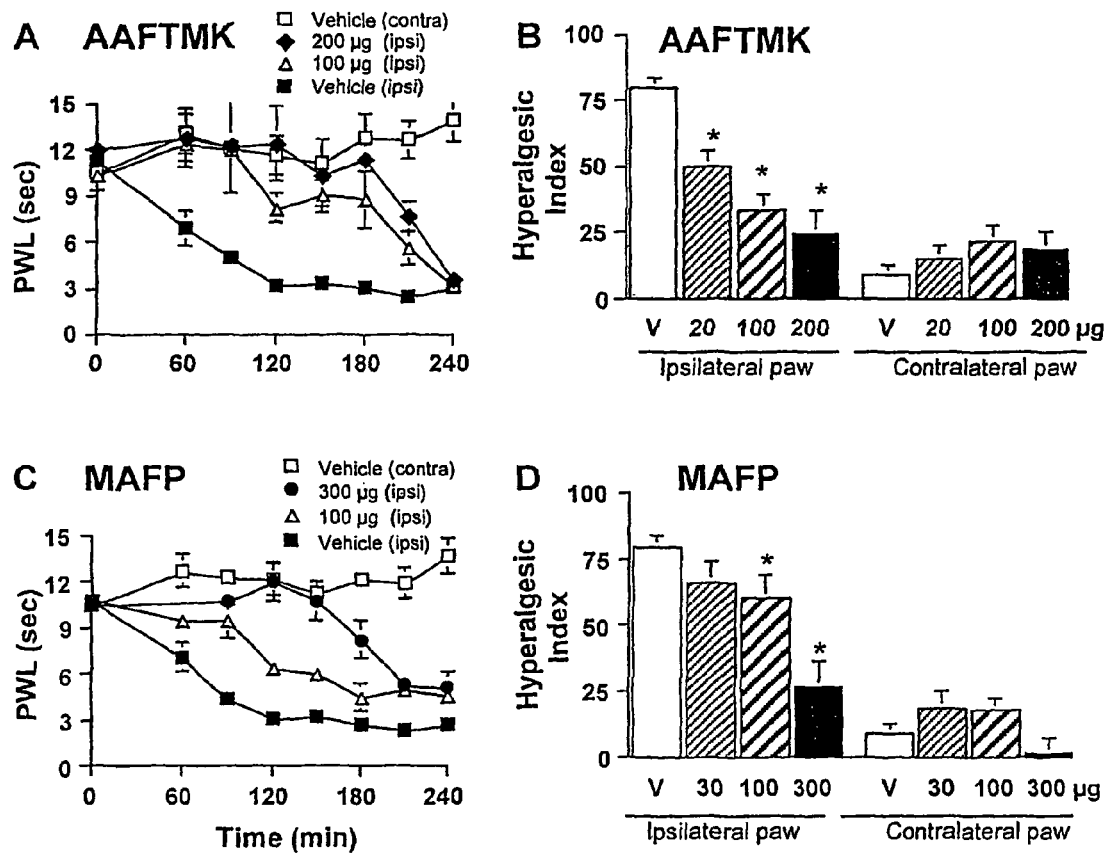
FIG. 1. Thermal escape latency (PWL) plotted versus time after injection of carrageenan into plantar face of left hind paw of rats pretreated (−10 mm) with intrathecal (IT) $PLA_2$ inhibitors, as follows: A: arachidonoyl trifluoromethylketone (AATFMK) (200 μg; closed diamonds and 100 μg; open triangles) and C: methyl arachidonyl fluorophosphonate (MAFP) (300 μg; closed circle and 100 μg; open triangles). The control group received paw carrageenan and IT vehicle. The paw withdrawal latency (PWL) for the inflamed paw (ipsi, closed squares) and non-inflamed paw (contra, open squares) is shown. Hyperalgesic index calculated over time from T=0 to T=180 min after different doses of IT B: ATFMK and D: MAFP. Each time point and bar represents the average and SEM for 4-6 rats and (*) represents P<0.05 versus vehicle treated carrageenan injected group (ipsilateral paw values).

A. PLA$_2$ Activity in the Central Nervous System.

The invention provides potent inhibitors of PLA$_2$, and methods for use of the inhibitory compounds. In the latter respect, it has been discovered that, although mRNA and protein levels of PLA$_2$ are not detectably upregulated in response to inflammatory signals, PLA$_2$ is nonetheless active in the spinal cord, and is causatively related to hyperalgesia. Targeting PLA$_2$ activity thus provides a new method for treating general inflammation and pain, as well as hyperalgesia (pain experienced through hypersensitivity to stimulus).

PLA$_2$ is the name for the class of lipolytic enzymes that hydrolyze the acyl group from the sn-2 position of glycerophospholipids, generating free fatty acids and lysophospholipids. The phospholipase A$_2$ superfamily of enzymes consists of two large branches, the histidine and serine PLA$_2$'s. The histidine PLA$_2$'s are similar small, secreted, Ca$^{2+}$-dependent enzymes that utilize a nucleophilic water molecule activated by the active site Ca$^{2+}$, aspartates, and especially a catalytic histidine (Groups I-III, V, IX-XIV). The other branch of the superfamily is composed of larger, typically cytosolic enzymes that utilize a nucleophilic serine (Groups IV and VI-VII).

Cytosolic PLA$_2$ (cPLA$_2$) has a strong preference for arachidonic acid at the sn-2 position of phospholipids and this observed in vitro preference has been shown to have physiological significance in the release of arachidonic acid and production of prostaglandins in vivo. In contrast, calcium-independent $PLA_2$ ($iPLA_2$) has no significant fatty acid specificity and its main function is believed to in membrane remodeling, although it is also believed to play a role both in arachidonic acid release and in leukotriene synthesis.

$PLA_2$ provides the cyclooxygenase enzymes (COX-1 and COX-2) with arachidonic acid, a required substrate for COX enzyme function in vivo. $cPLA_2$ is the principal provider of free lysophospholipid and arachidonic acid, the precursors of platelet activating factor (PAF) and eicosanoids, respectively. $cPLA_2$-stimulated production of arachidonic acid provides an intracellular intermediate for lipopolysaccharide (LPS) mediated production of prostaglandins. In particular, the arachidonic acid can be made directly into $PGE_2$ or can be used to transcriptionally upregulate the levels of $PLA_2$ available for production of prostaglandins (such as $PGE_2$), which serve as mediators of inflammation and pain.

In addition to supplying substrate for the COX-pathway, it has been shown that arachidonic acid liberated by $PLA_2$ may play additional roles in augmenting nociception. For example, arachidonic acid potentiates NMDA receptor currents and thus amplifies glutamate-mediated increases in intracellular calcium concentration by binding to sites on the NMDA-receptor, or by modifying the receptor's lipid environment. In addition, isoprostanes, a novel class of eicosanoids, are primarily formed by peroxidation of arachidonic acid in a non-COX dependent fashion. Isoprostanes act to sensitize rat sensory neurons thereby reducing mechanical and thermal withdrawal thresholds.

B. Role of $PLA_2$ in CNS Mediated Inflammatory Processes

In contrast to current belief in the art, $PLA_2$ expression in the spinal cord plays a significant role in spinally mediated inflammation, pain and hyperalgesia. Further, inhibition of $PLA_2$ activity in the CNS significantly decreases hyperalgesic responses in animals (rat paw edema model), and can abrogate production of $PGE_2$.

Expression of six $PLA_2$ enzymes, Groups IB, IIA, IIC, IVA, V and VI occurs in the spinal cord (as confirmed by Q-PCR in Example 5). Groups IVA and VI (referred to herein as $cPLA_2$ and $iPLA_2$, respectively) are the most highly expressed, showing over a 16-fold expression difference in comparison to the secretory $PLA_2$s ($sPLA_2$). Of the $sPLA_2$s, Group V shows the lowest expression having 200-fold less message than IB, IIA or IIC and fully four orders of magnitude less message than IVA or VI (data not shown).

Neither mRNA nor protein expression appear to be upregulated in response to local inflammation (Example 5); therefore, the major regulation of $cPLA_2$ activity is believed to be through translocation of the enzyme from the cytosol to the membrane subsequent to increases in intracellular calcium levels rather than through changes in protein expression. In addition to activation through translocation, $cPLA_2$ activity has also been shown to increase modestly following phosphorylation by MAPK proteins, although phosphorylation alone is not sufficient for arachodonic acid release.

Whatever the mechanism of $PLA_2$ activation in any particular cell or context, the biological responses to $PLA_2$ inhibition observed in connection with this invention appear to be due to a decrease in spinal facilitation rather than an anti-inflammatory action at the periphery since no decrease in paw edema was observed with decreased hyperalgesia following intrathecal administration of a $PLA_2$ inhibitor. Furthermore, intraperitoneal administration of the same amount of $PLA_2$ inhibitor that was given intrathecally had no effect on the carrageenan-induced thermal hyperalgesia.

As demonstrated in Examples 6 and 7 and summarized in Table I, $cPLA_2$ and $iPLA_2$ activity in rat spinal cord can be decreased by $PLA_2$ inhibitors. Intrathecal administration of the $cPLA_2$ and $iPLA_2$ inhibitors methyl arachidonyl fluororphosphonate (MAFP) and arachidonyl trifluoromethylketone (AATFMK) dose dependently prevented thermal hyperalgesia induced by injection of carrageenan into the hind paw as well as formalin induced flinching, with no effect on normal motor function (see also, Examples 2 and 3):

TABLE 1

Effect of Existing $PLA_2$ Inhibitors on Spontaneous Movement[a]

| Agent | Number of counts | N |
|---|---|---|
| Saline | 367 ± 45 | 6 |
| Vehicle | 306 ± 36 | 6 |
| AATFMK | 298 ± 41 | 6 |
| MAFP | 311 ± 40 | 6 |
| BEL[b] | 212 ± 32 | 6 |

[a]Spontaneous movement during 60 minutes after IT injection of saline, vehicle or $PLA_2$ inhibitors. Movement was quantified using the automated flinch counting device with the difference that no formalin was injected into the paw. Animals were acclimatized on the device and measurements started 10 minutes after IT administration of vehicle or drug.

[b]Intrathecal injection of the specific Group VI $iPLA_2$ inhibitor bromoenol lactone (BEL) reduced formalin induced flinching, but also suppressed spontaneous movement, possibly due to a sedation/motor dysfunction.

In contrast, although the COX enzymes are crucial to prostaglandin synthesis and their inhibition prior to injury has been shown to decrease hyperalgesia, IT administration of COX inhibitors after the onset of hyperalgesia cannot rescue hyperalgesic behavior (although partial mitigation of hyperalgesia is possible with IT AATFMK administered following the onset of inflammation). Thus, the inhibitory effect observed, coupled with the capacity of the inhibitors tested to clearly reduce $PLA_2$ activity in spinal homogenates (Examples 6 and 7), is strongly tied to modulation of $PLA_2$ activity.

C. Methods for Inhibition of $PLA_2$ in the CNS.

1. Activity of Existing $PLA_2$ Inhibitors.

As demonstrated above, known $PLA_2$ inhibitors (e.g., AATFMK and MAFP) have activity in the CNS. Other $PLA_2$ inhibitors are known to be active in a variety of mammalian cells (e.g., fatty acid tricarbonyl and trifluoromethyl ketones, as well as large-molecule pyrrolidine-based inhibitors), and so may also be active in spinal cord cells. However, many such inhibitors are neither reversible in their effect, nor are they entirely specific for $PLA_2$. Thus, while these inhibitors could inhibit spinally-mediated $PLA_2$ activity, better results will be obtainable with the specific and reversible $PLA_2$ inhibitors of the invention.

2. Novel 2-oxoamide $PLA_2$ Inhibitors: Activity and Structure.

A novel class of potent human $PLA_2$ inhibitors has been developed. These inhibitors contain the 2-oxoamide functionality and are described by Formula I:

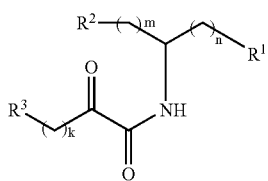

(I)

wherein

R$^1$ is any acidic group, such as a carboxyl, phosphate, phosphinate, sulfate, sulfonate, or tetrazolyl group; and, R$_2$, R$_3$ is any aromatic, heterocyclic, or carbocyclic group or a linear or branched, saturated or unsaturated alkyl, alkenyl, or alkynyl chain;

n≧0, m≧0, k≧0.

Based on the inhibition activity studies whose data are summarized in Tables 2-5 below, preferred PLA$_2$ inhibitors are those which possess characteristics including, without limitation, one or more of the following:

(1) all are hydrophobic 2-oxoamides produced according to general synthesis scheme (1) described in the following section of this disclosure;

(2) the R$_2$ side chain substituents may be α-, β-, γ-, δ-, and ε-amino acids;

(3) R$_3$ will possess more than 3 carbons, and preferably more than 6, and most preferably greater than 10 carbons in length;

(4) the free carboxy moiety is preferably preserved (but see, (8) below);

(5) the ether side chains will not be increased in length, if at all, by more than about 11 carbons;

(6) inhibitors having distances between the carboxy moiety and the oxoamide side chain comparable to the distance of the δ- or γ-norleucines from the carboxy group in the norleucine compounds are preferred, and the δ- and γ-norleucine variants are particularly preferred;

(7) methylenes may be added to the R$_3$ side chain;

(8) polar substitutents may be substituted for the free carboxy moiety of the inhibitors of the invention;

(9) for inhibition of cPLA$_2$ in particular, the molecule may be negatively charged.

Among the compounds tested, a long-chain 2-oxoamide containing L-γ-norleucine was one of the most potent inhibitors, causing a 50% decrease in cPLA$_2$ activity at 0.009 mole fraction (compound "OA4"; see, Tables 2 and 3, as well as Examples 2 and 7). All of the data above are provided with respect to X$_f$(50), which is the mole fraction of inhibitor in the total substrate interface required to inhibit the enzyme by 50%. Almost all inhibitors of PLA$_2$'s partition into the phospholipid surface, because they usually have a hydrophobic nature that helps them bind to the active site of the PLA$_2$. When these inhibitors partition into the surface, an important physical effect called surface dilution comes into play. In this case, the strength of the interaction of PLA$_2$ and an inhibitor depends not on the bulk concentration of the inhibitor (molar units), but on the surface concentration of the inhibitor (mole fraction units).

Figure 12:
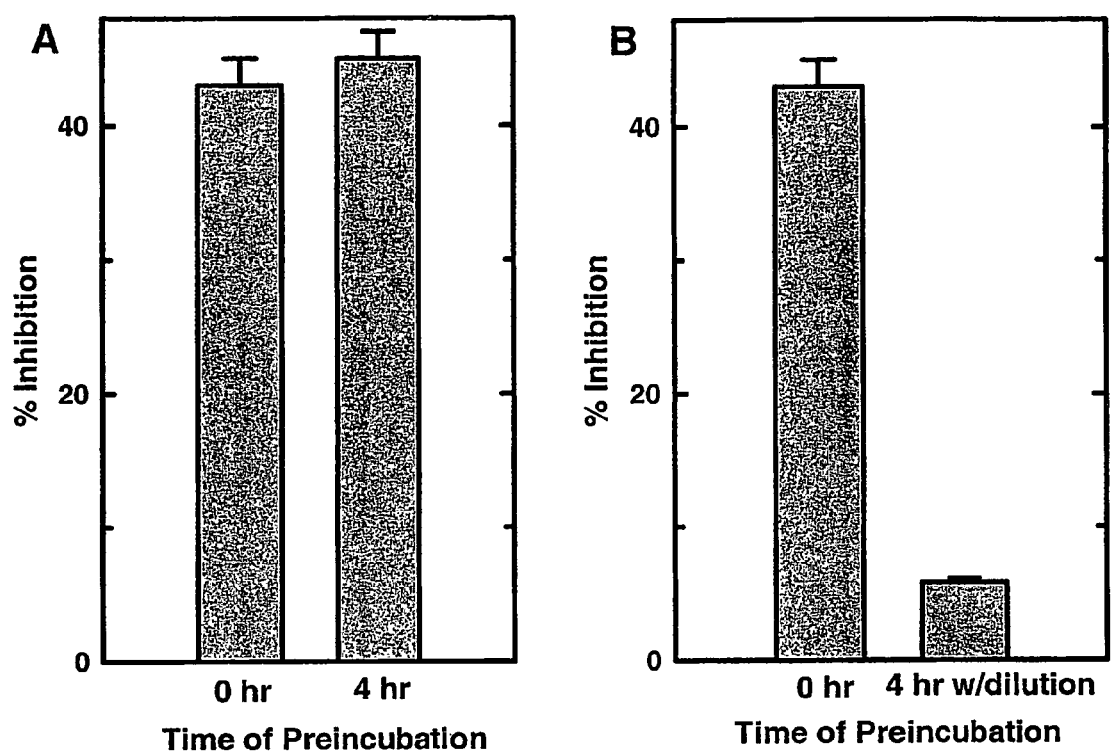
FIG. 12. A) The activity of cPLA$_2$ was tested on mixed micelles composed of TX-100 (400 µM, 1-palmitoyl-2-(1-[$^{14}$C])-arachidonoyl PC (97 µM, 100,000 cpm) and PIP$_2$ (3 µM, 0.6 mole %). The micelles also contained a final concentration of 0.005 mole fraction of OA4 (20 µM). cPLA$_2$ was first preincubated with OA4 (20 µM) for 0 or 4 hours before it was added to the substrate-containing solution that also contained OA4 (20 µM). B) The activity of cPLA$_2$ was tested on mixed micelles composed of TX-100 (400 µM, 1-palmitoyl-2-(1-[$^{14}$C])-arachidonoyl PC (97 µM, 100,000 cpm) and PIP$_2$ (3 µM, 0.6 mole %). The micelles also contained a final concentration of 0.005 mole fraction of OA4 (20 µM). cPLA$_2$ was first preincubated with OA4 (20 µM) for 0 or 4 hours before it was added to the substrate-containing solution that contained no additional OA4. This resulted in a final concentration for OA4 of 0.0005 mole fraction (2 µM).

The activity of several of the compounds synthesized and evaluated is summarized in the following Tables, and demonstrate that the compounds of the invention are potent PLA$_2$ inhibitors. As shown in FIGS. 12A and 12B, the inhibitory effect exhibited is fully reversible, making the inhibitory compounds of the invention particularly attractive candidates for use in therapeutic applications.

TABLE 2

Identities, chemical structures, and inhibitory potencies of various 2-oxo-amide compounds towards iPLA$_2$, N.D. signifies that the X$_f$(50) values were not able to be determined because the compounds are poor inhibitors. N/A signifies that an X$_f$(50) value is given for the compound.

| Number | Structure | X$_f$(50) (mole fraction) | Highest Conc. (mole fraction) w/ % Inhibition |
|---|---|---|---|
| OA1 | 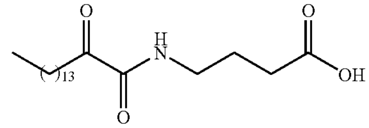 | 0.017 ± 0.009 | N/A |
| OA2 | 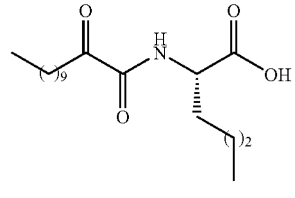 | N.D. | 0.091; 60% |
| OA3 | 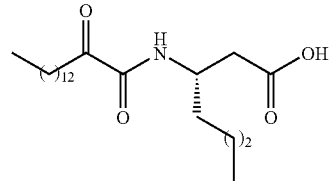 | 0.027 ± 0.004 | N/A |

TABLE 2-continued

Identities, chemical structures, and inhibitory potencies of various 2-oxo-amide compounds towards iPLA$_2$. N.D. signifies that the X$_I$(50) values were not able to be determined because the compounds are poor inhibitors. N/A signifies that an X$_I$(50) value is given for the compound.

| Number | Structure | X$_I$(50) (mole fraction) | Highest Conc. (mole fraction) w/ % Inhibition |
|---|---|---|---|
| OA4 | 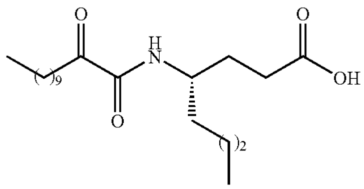 | 0.009 ± 0.004 | N/A |
| OA5 | 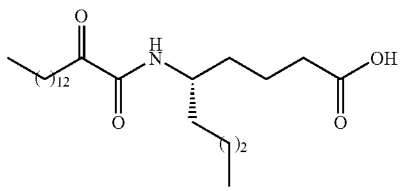 | 0.008 ± 0.003 | N/A |
| OA6 | 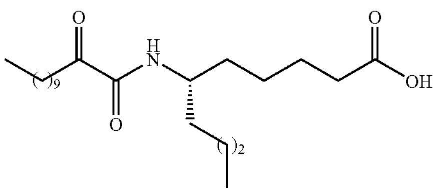 | 0.018 ± 0.009 | N/A |
| OA7 | 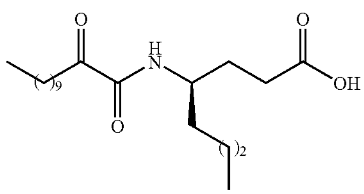 | 0.068 ± 0.005 | N/A |
| OA8 | 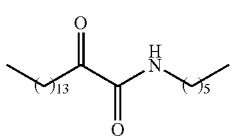 | N.D. | 0.02; 22% ± 7% |
| OA9 | 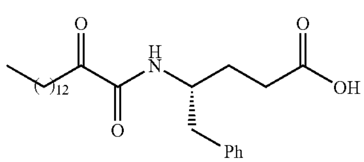 | 0.035 ± 0.016 | N/A |
| OA10 | 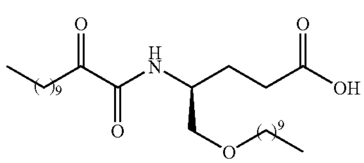 | 0.045 ± 0.007 | N/A |
| OA11 | 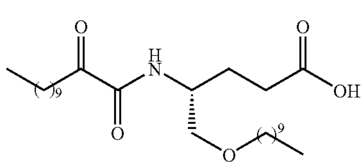 | 0.047 ± 0.006 | N/A |

TABLE 2-continued

Identities, chemical structures, and inhibitory potencies of various 2-oxo-amide compounds towards iPLA$_2$. N.D. signifies that the X$_I$(50) values were not able to be determined because the compounds are poor inhibitors. N/A signifies that an X$_I$(50) value is given for the compound.

| Number | Structure | X$_I$(50) (mole fraction) | Highest Conc. (mole fraction) w/ % Inhibition |
|---|---|---|---|
| OA12 | 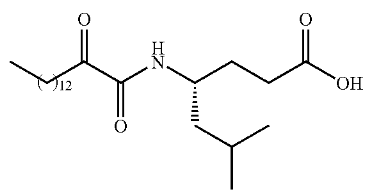 | 0.017 ± 0.006 | N/A |
| OA13 | 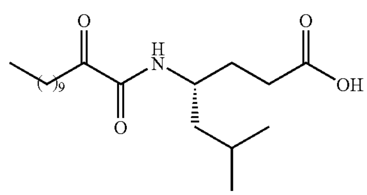 | 0.033 ± 0.013 | N/A |
| OA14 | 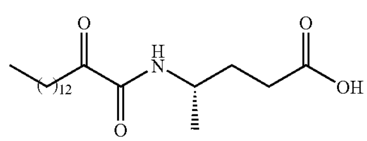 | 0.021 ± 0.006 | N/A |
| OA15 | 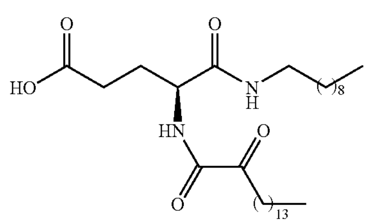 | 0.044 ± 0.007 | N/A |
| OA16 | 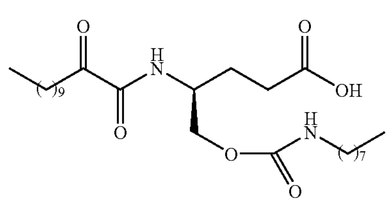 | N.D. | 0.091, 60% |
| OA17 | 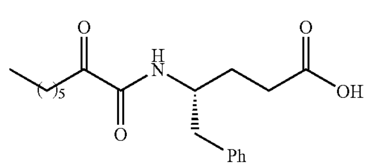 | N.D. | 0.091; 24% |
| OA18 | 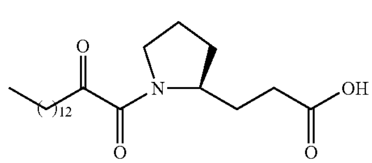 | N.D. | 0.091; 24% |

TABLE 3

Identities, chemical structures, and inhibitory potencies of various 2-oxo-amide compounds towards iPLA$_2$. N.D. signifies that the X$_f$(50) values were not able to be determined because the compounds are poor inhibitors or the stock concentrations do not permit a full dose dependent analysis. N/A signifies that an X$_f$(50) value is given for the compound.

| Number | Structure | X$_f$(50) (mole fraction) | Highest Conc. (mole fraction) w/ % inhibition |
|---|---|---|---|
| OA19 | (structure) | 0.0158 ± .0009 | N/A |
| OA20 | (structure) | N.D. | 0.091: 55% ± 4% |
| OA21 | (structure) | N.D. | 0.020: 38% ± 6% |
| OA22 | (structure) | N.D. | 0.020: 31% ± 6% |
| OA23 | (structure) | N.D. | 0.020: 43% ± 4% |
| OA24 | (structure) | N.D. | 0.020: 60% ± 6% |

TABLE 4

Identities, chemical structures and inhibitory potencies of various 2-oxo-amide compounds towards both iPLA$_2$ and cPLA$_2$. N.D. signifies that the X$_f$(50) values were not able to be determined because the compounds are poor inhibitors. N/A signifies that an X$_f$(50) value is given for the compound.

| Number | Structure | X$_f$(50) (mole fraction) | Highest Conc. (mole fraction w/ % Inhibition |
|---|---|---|---|
| OA25 | (structure) | C PLA$_2$: N.D. I PLA$_2$: 0.0142 ± 0.0004 | cPLA$_2$: 0.091: 41% iPLA$_2$: N/A |

TABLE 4-continued

Indentities, chemical structures and inhibitory potencies of various 2-oxo-amide compounds towards both iPLA$_2$ and cPLA$_2$. N.D. signifies that the X$_I$(50) values were not able to be determined because the compounds are poor inhibitors. N/A signifies that an X$_I$(50) value is given for the compound.

| Number | Structure | X$_I$(50) (mole fraction) | Highest Conc. (mole fraction w/ % Inhibition) |
|---|---|---|---|
| OA26 | 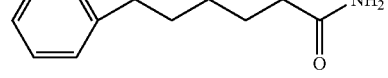 | cPLA$_2$: 0.028 ± 0.017<br>iPLA$_2$: 0.018 ± 0.002 | cPLA$_2$: N/A<br>iPLA$_2$: N/A |

TABLE 5

Indentities and chemical structures of 2-oxo-amide compounds which show no inhibition of either cPLA$_2$ or iPLA$_2$.

| Number | Structure |
|---|---|
| OA27 | 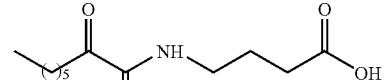 |
| OA28 | 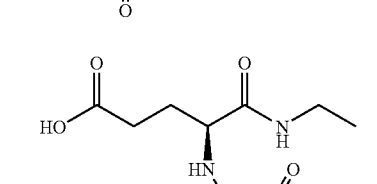 |
| OA29 | 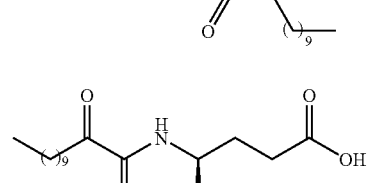 |
| OA30 | 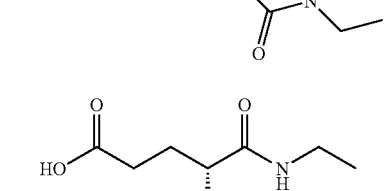 |
| OA31 | 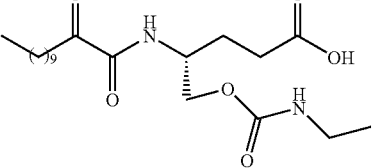 |
| OA32 | 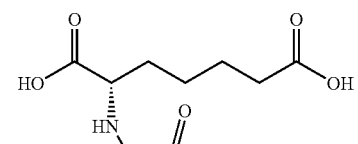 |
| OA33 | 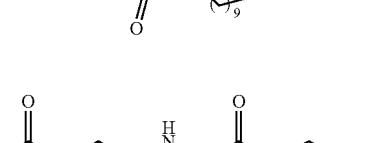 |
| OA34 | 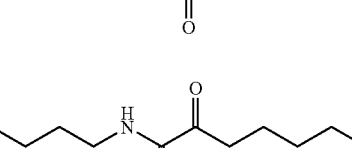 |
| OA35 | 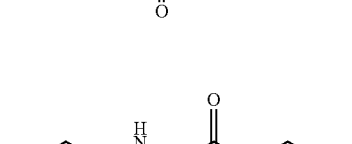 |
| OA36 | |

TABLE 5-continued

Indentities and chemical structures of 2-oxo-amide compounds which show no inhibition of either cPLA$_2$ or iPLA$_2$.

| Number | Structure |
|---|---|
| OA37 | [structure: 2-oxoacyl-proline with propanoic acid, (CH$_2$)$_{12}$ chain] |
| OA38 | [structure: amide with (CH$_2$)$_{14}$ chain and butanoic acid] |

These data demonstrate both the necessary and desirable characteristics of the PLA$_2$ inhibitors of the invention. For example, the length of the R$_3$ substituent is significant. Using leucine and phenylalanine variants, the role of the saturated chain length (R$_3$ position, see Formula I) off the 2-oxo acid moiety (13 carbons) was explored. When the length was shortened to 6 carbons or 10 carbons the potency went down about 4-fold and 2-fold respectively. OA29, a γ-carbamate with a shorter R$_3$ substituent, did not inhibit cPLA$_2$ (Table 5), while a longer chain at the R$_3$ position produces a moderate level of inhibition (OA15, Table 2). This same effect is seen in comparison of the activities of OA28 and OA1 (in Table 5 and Table 2, respectively).

While the invention is not intended to be limited by its mechanism of action, it is possible that partitioning to the lipid micelles is affected by less hydrophobic shortened acyl chains or, more likely, results from a weaker interaction with the deep hydrophobic active site of cPLA$_2$. This is suggested by the lack of inhibition of cPLA$_2$ by compounds with an R$_3$ phenyl substituent linked to the 2-oxoamide by 4- or 3-methylene groups (OA35 and OA36, Table 5). These compounds have a shorter substituent that is also bulkier, which might also affect their activity. As expected, the carboxymethyl ester versions of these two compounds also do not inhibit cPLA$_2$ (OA20 and OA34, Table 3 and Table 5, respectively).

Further, activity appears to depend in part on the presence of the free carboxy group (see Table 2 and compare data for OA1 and OA8). Inhibitory potency can alternatively be enhanced to a degree by addition of relatively polar substituents to the molecule. This phenomenon is demonstrated by OA25 (Table 5), which has a lactone in place of the carboxy and γ-side chain, and is therefore uncharged. As would be expected, OA25 is a fairly poor inhibitor of cPLA$_2$, but does possess some inhibitory activity at 0.091 mole fraction. In contrast, OA19, the carboxymethyl ester (Table 3), exhibits no inhibitory activity. Further illustration of this phenomenon is provided by OA26 (Table 5), which is a carboxymethyl ester variant of the free carboxy-containing carbamate OA30 (Table 5). OA30 does not inhibit cPLA$_2$, while OA26 does, notwithstanding the absence therein of a free carboxy moiety. OA26's activity is most likely due to incompatibility between the polarities of the carbamate side chain and the free carboxy group with the cPLA$_2$ active site, while the polarity of the carbamate and carboxymethyl ester are better suited.

Therefore, taking into account the composition of the cPLA$_2$ active site, it is possible to substitute polar substitutents for the free carboxy moiety of the inhibitors of the invention, while retaining a degree of inhibitory activity. As such, these polar substituted molecules are within the scope of the invention. Nonetheless, inhibitor molecules having the free carboxy moiety are generally preferred.

Activity in cPLA$_2$ inhibitors is also enhanced by the existence of a negative charge in the inhibitor, as indicated by the lack of inhibition provided by a variant of OA1 that contained a carboxymethyl ester in place of the free carboxy (OA19, Table 3). OA19 has no measurable inhibition against cPLA$_2$ at up to 0.091 mole fraction.

Potency is also enhanced by an increase in relative distance between the oxoamide group and the carboxy group (see, Table 2, comparison of activity in α-, β-, γ-, δ-, and ε-amino acid variants of OA4 (OA2, OA3, OA4, OA5, and OA6, respectively). In particular, as the carboxy moiety is moved further away from the norleucine side chain, the inhibitory potency increases. For example, α-amino acid variant, OA2, is a relatively poor inhibitor (around 7-fold less potent than OA4). The β-norleucine displays better inhibitory activity; i.e., around 3-fold less potency than OA4. The δ-norleucine has inhibitory activity essentially equivalent to that of OA4. However, consistent with the leveling off of inhibitory potency from the δ- to γ-norleucines, the ε-amino acid variant, OA6, was around 2-fold less potent than OA4 (Table 2). As such, inhibitors having distances between the carboxy moiety and the oxoamide moiety comparable to the distance of the δ- or γ-norleucines from the carboxy group are preferred, and the δ- and γ-norleucine variants are particularly preferred.

In addition to use of the δ- or γ-norleucine variants, distance and hydrophobicity may be provided in the inhibitors of the invention by other modifications, which those of ordinary skill in the art may identify, such as the addition of one or more methylenes to increase hydrophobicity. For example, the R$_3$ substituent (see Formula I), varies from 9 methylenes in OA2, OA4 and OA6, to 12 methylenes in OA3 and OA5. As a longer R$_3$ substituent appears to benefit the inhibitory potency, a γ-norleucine with 12 methylenes at the R$_3$ position can be reasonably expected to be more potent that the 9 methylene γ-norleucine (OA4) or even the 12 methylene δ-norleucine (OA5).

Figure 13:
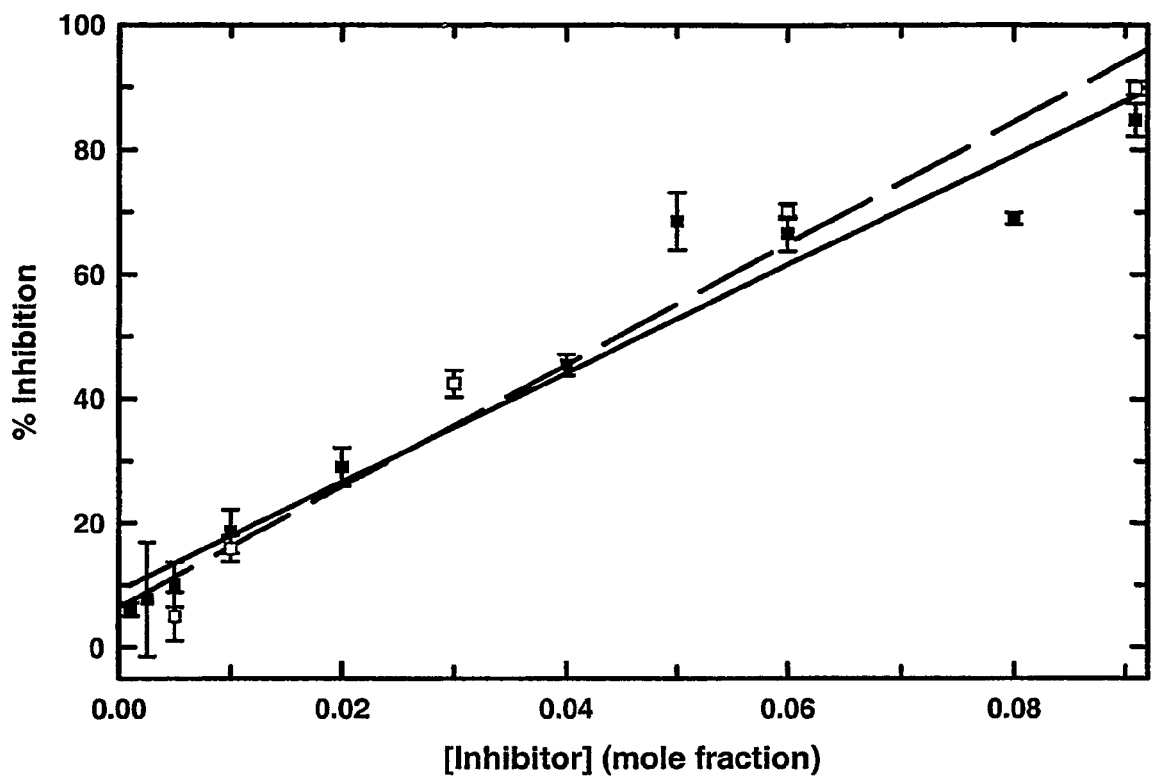
FIG. 13. The activity of cPLA2 was tested on mixed micelles composed of TX-100 (400 µM), 1-palmitoyl-2-(1-[$^{14}$C])-arachidonoyl PC (97 µM, 100,000 cpm) and PIP$_2$ (3 µM, 0.6 mole %). The surface concentration of OA10 (■) and OA11 (□) were separately increased as shown. The data were fit to linear least squares functions (OA10, dashed line and OA11, solid line). The lines give values for the OA11 X$_f$(50) of 0.047±0.006 and for the OA10 X$_f$(50) of 0.045±0.007.

However, the data also indicate a limitation on variation in the inhibitory compounds' structures. A significant overall increased length of the ether side chains may not be tolerated by the cPLA$_2$ active site in particular. While the L-γ-norleucine 2-oxoamide (OA4) is quite potent against cPLA$_2$ activity, substitution of a longer (11 carbon) ether containing side chain in place of the norleucine side chain results in a 5-fold decrease in inhibitory potency by both stereoisomers (FIG. 13). The linear (vs logarithmic) shape of the data indicates a poor inhibition which is confirmed by the X$_f$(50) for both enantiomers at around 0.045 mole fraction, suggesting that the cPLA$_2$ active site may have some intolerance for the more polar heteroatoms at this position. This hypothesis is further supported by the lack of inhibition by side chains containing a carbamate (e.g., OA16, OA30 and OA32, Tables 2 and 4) or amide (e.g., OA31 and OA29, Table 4), which had essentially no measurable inhibition of cPLA$_2$.

3. Synthesis of Novel 2-oxoamide PLA$_2$ Inhibitors.

General structures and synthesis schemes for the compounds described in the foregoing Tables, and others, are provided below. Synthesis of a number of representative simple primary and secondary 2-oxoamides, as well as four derivatives containing a free carboxyl group, is shown. Synthesis of a specific, representative inhibitory compound, OA4, is also detailed in Example 8.

General scheme for the synthesis of 2-oxo-amides containing a carboxyl group

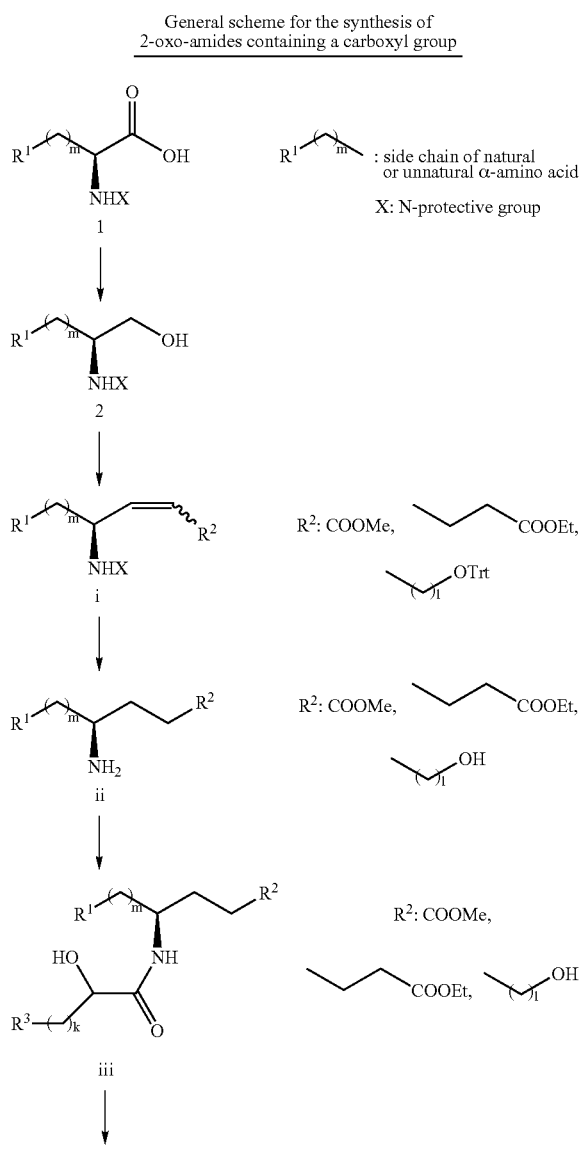

Synthesis of the inhibitors of the invention can be achieved beginning with the first and second steps outlined above in Scheme 1, and as repeated below in Scheme 2. In both schemes, N-protected amino alcohols 1 are prepared from the corresponding natural or unnatural α-amino acids by the mixed anhydride-$NaBH_4$ or the acyl fluoride-$NaBH_4$ method. Alcohols 1 are oxidized to the corresponding aldehydes by NaOCl in the presence of a catalytic amount of 4-acetamido-2,2,6,6-tetramethylpiperidine-1-yloxy free radical (AcNH-TEMPO) and the aldehydes 2 are directly used in the next step without any purification.

In Scheme 1, step (i) generally represents alternative Steps 3, 4 and/or 5, and equivalents, as depicted in Scheme 2. Step (ii) generally represents Steps 6, 7 and/or 8, and equivalents, as depicted in Scheme 2. Step (iii) generally represents Step 9, and equivalents, as depicted in Scheme 2, while step (iv) is collectively representative of the steps for alternative routes of synthesis depicted in Schemes 3-9.

There are three routes for the synthesis of γ-amino acid based 2-oxoamide inhibitors depending on the ylide and the N-protecting group used (Scheme 2). Wittig reaction of Boc-protected amino aldehydes 2 with benzyl or methyl (triphenylphosphoranylide)acetate leads to α,β-unsaturated esters 3 and 4. The Boc group is removed, and the amino component is coupled with 2-hydroxy acids using 1-(3-dimethylaminopropyl)-3-ethyl carbodiimide (WSCI) in the presence of hydroxybenzotriazole (HOBt). Catalytic hydrogenation of 6 and 7, combined with saponification in the case of 7, followed by oxidation with either PDC or NaOCl/AcNH-TEMPO leads to the target compounds 9. Z-Protected amino aldehydes 2 are treated with tert-butyl triphenylphosphoranylidene)acetate to give compound 5. After catalytic hydrogenation the amino component is coupled with 2-hydroxy acids by the WSCI/HOBt method. Oxidation of 8 followed by removal of tert-butyl group with $CF_3COOH$ leads to compounds 9.

Scheme 2. Three routes for the synthesis of γ-amino acid based 2-oxoamide inhibitors.

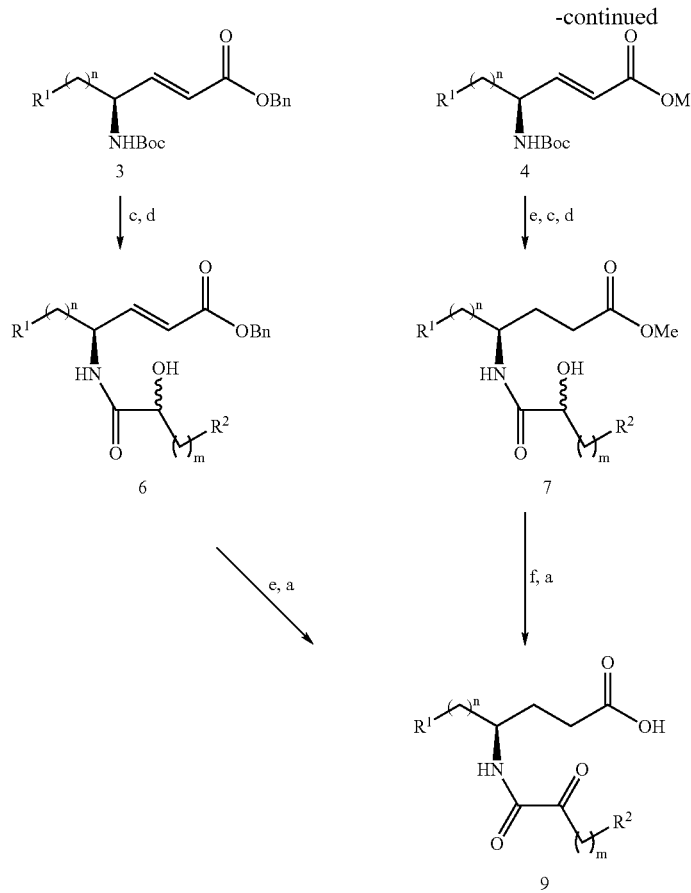
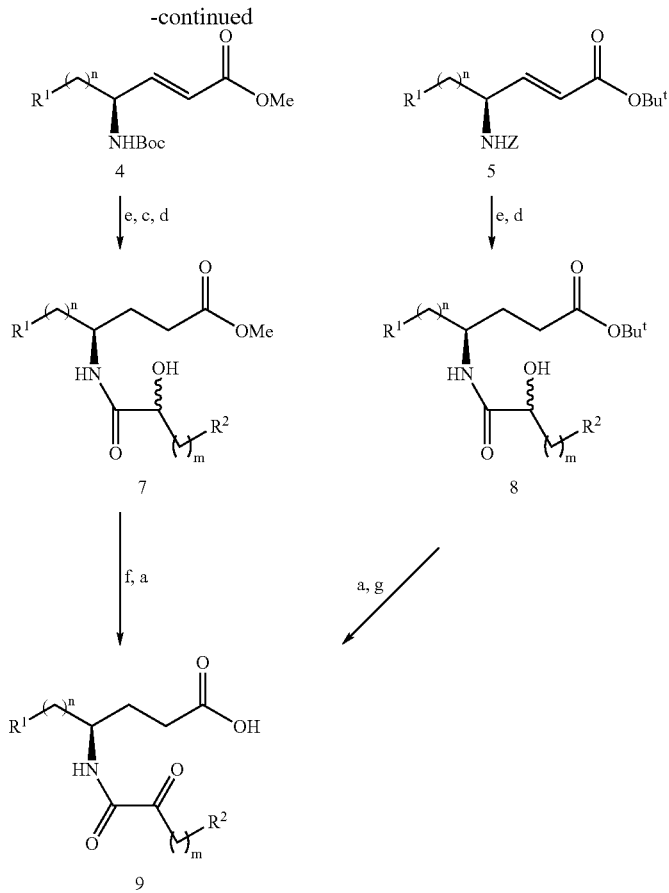

Reagents and conditions: (a) NaOCl, AcNH-TEMPO, NaBr, NaHCO$_3$, toluene/EtOAc/H$_2$O 3:3:0.5, −5° C.; (b) Ph$_3$P=CHCO$_2$Y, THF, reflux; (c) 4N HCl/Et$_2$O; (d) R$^2$(CH$_2$)$_m$CHOHCO$_2$H, WSCI, HOBt; (e) H$_2$, 10% Pd/C; (f) 1N NaOH, dioxane/H$_2$O 9:1; (g) 50% CF$_3$CO$_2$H/CH$_2$Cl$_2$.

For the synthesis of ε-amino acid based inhibitors, alcohols 1 are converted into aldehydes and reacted with triethyl phosphonocrotonate (Scheme 3). Catalytic hydrogenation of compounds 10, removal of the protecting group and coupling with 2-hydroxy acids gives compounds 11. Saponification, followed by oxidation, leads to compounds 12.

Scheme 3. Synthesis of ε-amino acid based 2-oxoamide inhibitors.

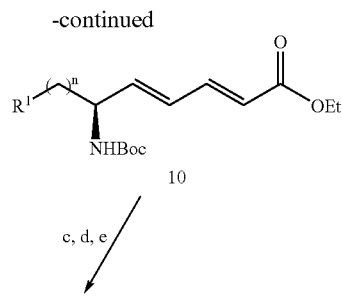

Reagents and conditions: (a) NaOCl, AcNH-TEMPO, NaBr, NaHCO$_3$, toluene/EtOAc/H$_2$O 3:3:0.5, −5° C.; (b) (EtO)$_2$P(=O)CH$_2$CH=CHCO$_2$Et, LiOH, THF; (c) H$_2$ 10% Pd/C; (d) 4N HCl/Et$_2$O; (e) R$^2$(CH$_2$)$_m$CHOHCO$_2$H, WSCI, HOBt; (f) 1N NaOH, dioxane/H$_2$O 9:1.

For the synthesis of α-amino acid based inhibitors, methyl esters of α-amino acids 13 are coupled with 2-hydroxy acids (Scheme 4). Saponification of 14, followed by oxidation, leading to compounds 15.

Scheme 4. Synthesis of α-amino acid based 2-oxoamide inhibitors.

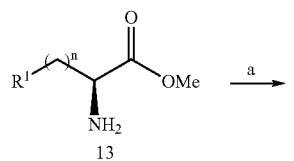
13

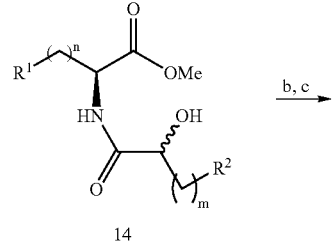
14

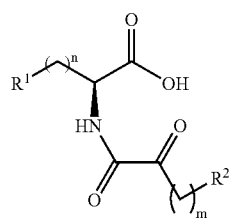
15

Reagents and conditions: (a) R²(CH₂)ₘCHOHCO₂H, WSCI, HOBt; (b) 1N NaOH, dioxane/H₂O 9:1; (c) NaOCl, AcNH-TEMPO, NaBr, NaHCO₃, toluene/EtOAc/H₂O 3:3: 0.5, −5° C.

Likewise, β-amino acid based 2-oxoamide inhibitors can be prepared from β-amino acid esters following the route depicted in Scheme 4 for α-amino acid based inhibitors. Alternatively, for the synthesis of β-amino acid based inhibitors, N-(tert-butoxycarbonyl)-phenylalaninol 16 may be used as a starting material. Compound 16 is oxidized and treated with alkylidene phosphoranes to produce compounds 17 (Scheme 5). Removal of the protecting group and coupling with 2-hydroxy acids leads to compounds 18, which are hydrogenated. The phenyl group is converted to carboxylic acid by oxidation with NaIO₄, RuCl₃ in MeCN, EtOAc, H₂O (1:1:8).

Scheme 5. Synthesis of β-amino acid based 2-oxoamide inhibitors.

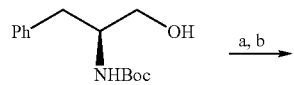
16

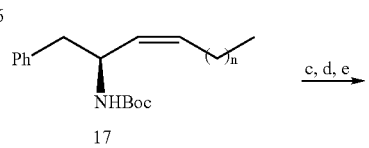
17

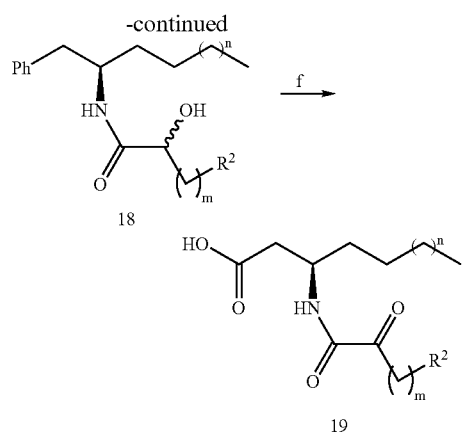

Reagents and conditions: (a) NaOCl, AcNH-TEMPO, NaBr, NaHCO₃, toluene/EtOAc/H₂O 3:3:0.5, −5° C.; (b) CH₃(CH₂)ₙCH₂P⁺Ph₃Br⁻, KHMDS, toluene, −78° C.; (c) H₂ 10% Pd/C; (d) 4N HCl/Et₂O; (e) R²(CH₂)ₘCHOHCO₂H, WSCI, HOBt; (f) NaIO₄, RuCl₃, MeCN/EtOAc/H₂O 1:1:8.

For the synthesis of δ-amino acid based inhibitors, Boc-protected amino alcohols 1 were oxidized and reacted with the ylide generated from Br⁻ Ph₃P⁺CH₂CH₂C₆H₅ (Scheme 6). Removal of the protecting group of 20 and coupling with 2-hydroxy acids led to compounds 21. After catalytic hydrogenation, oxidative conversion of the phenyl group to carboxylic acid led to compounds 22.

Scheme 6. Synthesis of δ-amino acid based 2-oxoamide inhibitors.

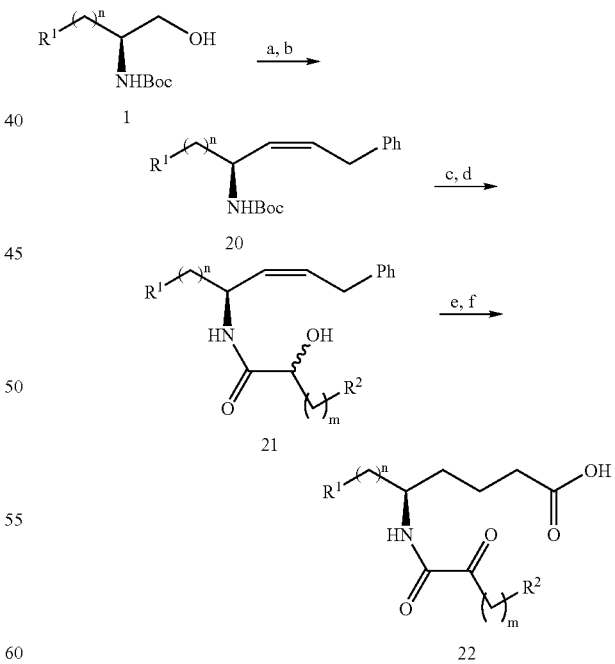

Reagents and conditions: (a) NaOCl, AcNH-TEMPO, NaBr, NaHCO₃, toluene/EtOAc/H₂O 3:3:0.5, −5° C.; (b) PhCH₂CH₂P⁺Ph₃Br⁻, KHMDS, toluene, −78° C.; (c) 4N HCl/Et₂O; (d) R²(CH₂)ₘCHOHCO₂H, WSCI, HOBt; (e) H₂ 10% Pd/C; (f) NaIO₄, RuCl₃, MeCN/EtOAc/H₂O 1:1:8.

The synthesis of inhibitors based on homologated amino acids may also be accomplished as depicted in Scheme 7. Boc-Protected amino aldehydes, produced from 1, are reacted with the ylides generated from I⁻Ph₃P⁺CH₂(CH₂)ₙOTr. Removal of the protecting group of 23 and coupling with 2-hydroxy acids leads to compounds 24. Catalytic hydrogenation and oxidation by NaOCl/AcNH-TEMPO in the presence of a phase-transfer catalyst leads to compounds 25.

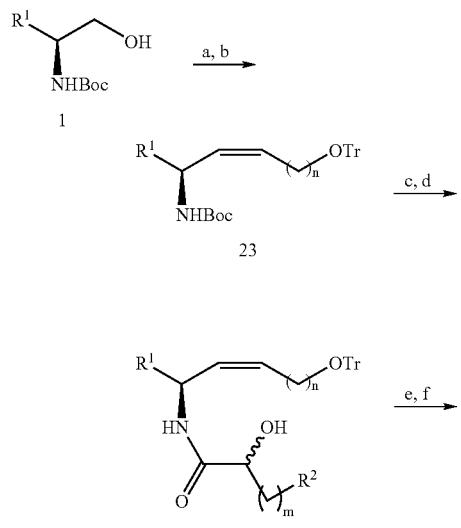

Reagents and conditions: (a) NaOCl, AcNH-TEMPO, NaBr, NaHCO₃, toluene/EtOAc/H₂O 3:3:0.5, −5° C.; (b) TrO(CH₂)ₙCH₂P⁺Ph₃I⁻, KHMDS, toluene, −78° C.; (c) 4N HCl/Et₂O; (d) R²(CH₂)ₘCHOHCO₂H, WSCI, HOBt; (e) H₂ 10% Pd/C; (f) NaOCl, AcNH-TEMPO, Bu₄N⁺HSO₄⁻, NaBr, NaHCO₃, CH₂Cl₂/H₂O, 0° C.

Glutamic acid based 2-oxoamides can be prepared as depicted in Schemes 8 and 9. γ-Methyl tert-butoxycarbonylglutamate 26 was coupled with amines by the WSCI/HOBt method. Removal of the protecting group and coupling with 2-hydroxy acids led to compounds 28. Compounds 29 were produced by saponification of 28 and oxidation with NaOCl/AcNH-TEMPO. Alcohol 30 was converted into carbamates 31 by treatment with alkyl isocyanates. Removal of the protecting group and coupling with 2-hydroxy acids led to compounds 32. Compounds 33 were produced by saponification of 32 and oxidation with NaOCl/AcNH-TEMPO.

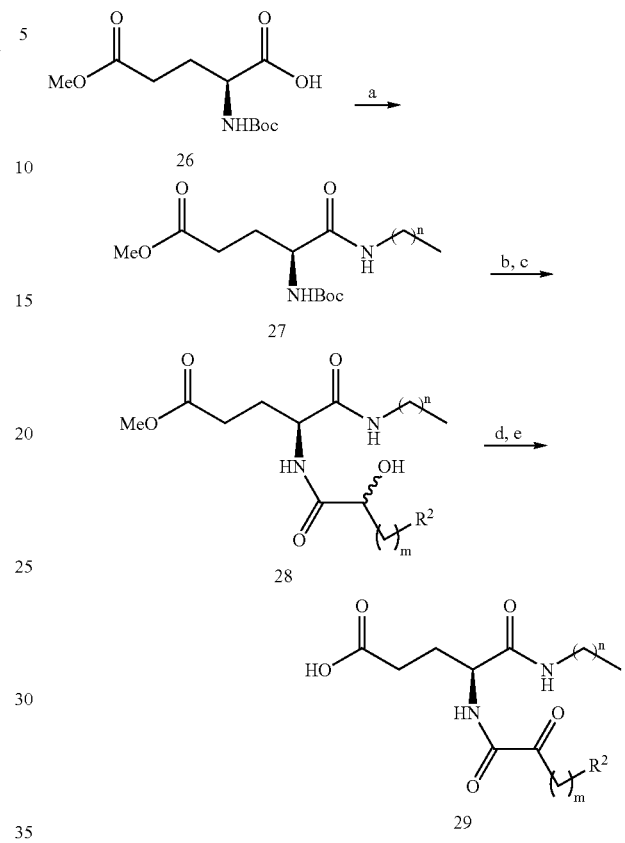

Reagents and conditions: (a) CH₃(CH₂)ₙNH₂, WSCI, HOBt; (b) 4N HCl/MeOH; (c) R²(CH₂)ₘCHOHCO₂H, WSCI, HOBt; (d) 1N NaOH/MeOH; (e) NaOCl, AcNH-TEMPO, NaBr, NaHCO₃, toluene/EtOAc/H₂O 3:3:0.5, 5° C.

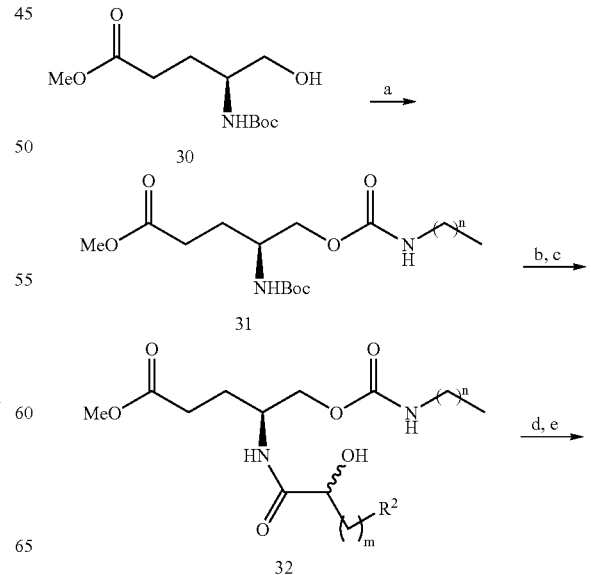

-continued

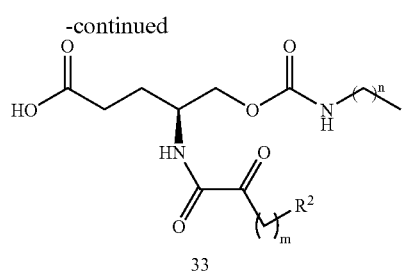
33

Reagents and conditions: (a) $CH_3(CH_2)_nNCO$, DMAP; (b) 4N HCl/MeOH; (c) $R^2(CH_2)_mCHOHCO_2H$, WSCI, HOBt; (d) 1N NaOH/MeOH; (e) NaOCl, AcNH-TEMPO, NaBr, $NaHCO_3$, toluene/EtOAc/$H_2O$ 3:3:0.5, −5° C.

Analytical Data for Particular Inhibitory Compounds (4R)-5-(Decyloxy)-4-[(2-oxododecanoyl)amino]pentanoic Acid (OA11)

$[\alpha]D$−16.2 (c 0.5 $CHCl_3$). 1H NMR: δ 7.24 (1H, d, CONH, J=9.4 Hz), 4.08 (1H, m, CHNH), 3.42 (4H, m, 2×$CH_2O$), 2.90 (2H, t, $CH_2COCO$, J=7.8 Hz) 2.39 (2H, t, $CH_2COOH$, J=7.0 Hz), 1.99 (2H, m, $CH_2CH_2COOH$), 1.58 (4H, m, $CH_2CH_2COCO$, $CH_2CH_2O$), 1.26 (28H, m, 14×$CH_2$), 0.88 (3H, t, J=6.0 Hz, $CH_3$).

13C NMR: δ 199.0, 178.4, 160.0, 71.6, 69.7, 48.7, 36.8, 31.8, 29.6, 29.4, 29.3, 29.0, 26.0, 23.1, 22.6, 14.1.

(3S)-(2-Oxo-pentadecanoylamino)-heptanoic Acid (OA3)

1H NMR: δ 7.31 (1H, d, J=9 Hz, NH), 4.20 (1H, m, CH), 2.91 (2H, t, J=7.8 Hz, $CH_2COCO$), 2.61 (2H, d, J=5 Hz, $CH_2COOH$), 1.60 (4H, m, 2×$CH_2$), 1.25 (24H, m, 12×$CH_2$), 0.88 (6H, t, J=6.8 Hz, 2×$CH_3$). 13C-NMR: δ 199.2, 176.4, 159.7, 46.1, 38.2, 36.8, 33.5, 31.9, 29.6, 29.4, 29.3, 29.0, 28.1, 23.1, 22.7, 22.3, 14.1, 13.9.

(5S)-5-(2-Oxopentadecanoylamino)-nonanoic Acid (OA5)

1H NMR: δ 6.73 (1H, d, J=9 Hz, NH), 3.87 (1H, m, CH), 2.92 (2H, t, J=7.8 Hz, $CH_2COCO$), 2.35 (2H, m, $CH_2COOH$), 1.72-1.46 (8H, m, 4×$CH_2$), 1.25 (24H, m, 12×$CH_2$), 0.88 (6H, t, J=6.8 Hz, 2×$CH_3$).

13C-NMR: δ 199.6, 178.3, 159.9, 49.3, 36.8, 34.6, 34.2, 33.4, 31.9, 29.6, 29.4, 29.3, 29.0, 27.9, 23.2, 22.7, 22.5, 20.9, 14.1, 13.9.

(4S)-4-(2-Oxopentadecanoylamino)-heptanoic Acid (OA14)

1H NMR: δ 6.93 (1H, d, J=9 Hz, NH), 4.03 (1H, m, CH), 2.91 (2H, t, J=7.8 Hz, $CH_2COCO$), 2.39 (2H, m, $CH_2COOH$), 1.85 (2H, m, $CH_2$), 1.59 (2H, m, $CH_2$), 1.25 (23H, m, 10×$CH_2$, $CH_3$), 0.88 (3H, t, J=6.7 Hz, $CH_3$). 13C-NMR: δ 199.4, 178.3, 159.7, 45.1, 36.7, 31.9, 31.3, 30.7, 29.6, 29.4, 29.3, 29.0, 23.1, 22.7, 20.7, 14.1.

(4R)-6-Methyl-4-(2-oxo-dodecanoylamino)-heptanoic Acid (OA13)

1H NMR: δ 6.83 (1H, d, J=9 Hz, N, 4.02 (1H, m, CH), 2.91 (2H, t, J=7.8 Hz, $CH_2COCO$), 2.36 (2H, m, $CH_2COOH$), 1.91 [3H, m, $CH_2$, $CH(CH_3)_2$], 1.59 (4H, m, 2×$CH_2$), 1.25 (14H, m, 7×$CH_2$), 0.91 (9H, t, J=6.8 Hz, 3×$CH_3$). 13C-NMR: δ 199.4, 178.4, 160.1, 47.4, 44.3, 36.8, 31.8, 30.7, 30.4, 29.5, 29.4, 29.3, 29.2, 29.0, 24.9, 23.2, 22.9, 22.6, 22.0, 14.1.

(6S)-6-(2-Oxo-dodecanoylamino)-decanoic Acid (OA6)

1H NMR: δ 6.72 (1H, d, J=9 Hz, NH), 3.85 (1H, m, CH), 2.90 (2H, t, J=7.8 Hz, $CH_2COCO$), 2.31 (2H, t, J=7.4 Hz, $CH_2COOH$), 1.78-1.23 (28H, m, 14×$CH_2$), 0.88 (6H, t, J=6.8 Hz, 2×$CH_3$). 13C-NMR: δ 199.7, 179.3, 159.8, 49.4, 36.8, 34.6, 33.7, 31.8, 29.5, 29.4, 29.3, 29.0, 27.9, 25.3, 24.4, 23.2, 22.6, 22.5, 14.1, 13.9.

(4R)-4-(2-Oxo-pentadecanoylamino)-5-phenyl-pentanoic Acid (OA9)

1H NMR: δ 7.33-7.14 (5H, m, $C_6H_5$), 6.97 (1H, d, J=9 Hz, NH), 4.20 (1H, m, CH), 2.86 (4H, m, $CH_2C_6H_5$, $CH_2COCO$), 2.37 (2H, t, J=7.2 Hz, $CH_2COOH$), 1.95 (1H, m, CHH), 1.81 (1H, m, CHH), 1.56 (2H, m, $CH_2$), 1.26 (20H, m, 10×$CH_2$), 0.89 (3H, t, J=6.8 Hz, $CH_3$). 13C-NMR: δ199.2, 178.0, 160.0, 136.9, 129.2, 128.6, 126.8, 50.3, 41.1, 36.7, 31.9, 30.7, 29.6, 29.4, 29.3, 29.0, 28.9, 23.1, 22.7, 14.1.

(2S)-2-(2-Oxo-pentadecanoylamino)-hexanoic Acid (OA2)

1H NMR: δ7.41 (1H, d, J=9 Hz, NH), 4.52 (1H, m, CH), 2.90 (2H, t, J=7.8 Hz, $CH_2COCO$), 2.00-1.56 (6H, m, 3×$CH_2$), 1.25 (16H, m, 8×$CH_2$), 0.88 (6H, 1, J=6.7 Hz, 2×$CH_3$). 13C-NMR: δ 198.5, 176.4, 159.9, 52.8, 36.8, 31.9, 29.6, 29.4, 29.3, 29.0, 27.4, 23.1, 22.7, 22.3, 14.1, 13.8.

(4R)-4-(2-Oxo-octanoylamino)-5-phenyl-pentanoic Acid (OA17)

1H NMR: δ7.38-7.14 (5H, m, $C_6H_5$), 6.95 (1H, d, J=9 Hz, NH), 4.20 (1H, m, CH), 2.86 (4H, m, $CH_2C_6H_5$, $CH_2COCO$), 2.37 (2H, t, J=7.4 Hz, $CH_2COOH$), 1.97 (1H, m, CHH), 1.78 (1H, m, CHH), 1.57 (2H, m, $CH_2$), 1.26 (6H, m, 3×$CH_2$), 0.87 (3H, t, J=6.8 Hz, $CH_3$). 13C-NMR: δ199.2, 177.6, 160.0, 136.9, 128.7, 128.1, 127.0, 50.3, 41.1, 36.7, 31.5, 28.7, 26.3, 22.4, 14.0.

(4R)-6-Methyl-4-(2-oxo-pentadecanoylamino)-heptanoic Acid (OA12)

1H NMR: δ 6.95 (1H, d, J=9.2 Hz, NH), 4.00 (1H, m, CH), 2.91 (2H, t, J=7.8 Hz, $CH_2COCO$), 2.30 (2H, m, $CH_2COOH$), 1.91 [3H, m, $CH_2$, $CH(CH_3)_2$], 1.59 (4H, m, 2×$CH_2$), 1.25 (20H, m, 10×$CH_2$), 0.91 (9H, t, J=6.8 Hz, 3×$CH_3$). 13C-NMR: δ 199.3, 178.8, 160.0, 47.3, 44.1, 36.8, 31.8, 31.1, 30.4, 29.5, 29.3, 29.2, 28.9, 24.7, 23.0, 22.9, 22.5, 21.9, 22.5, 13.9.

3-[1-(2-Oxo-pentadecanoyl)-pyrrolidin-2-yl]propionic Acid (OA18)

1H NMR: δ4.21 (1H, m, CH), 3.54 (2H, m, $CH_2NH$), 2.84 (2H, m, $CH_2COCO$), 2.35 (2H, m, $CH_2COOH$), 2.01-1.41 (8H, m, 4×$CH_2$), 1.25 (20H, m, 10×$CH_2$), 0.86 (3H, t, J=6.6 Hz, $CH_3$). 13C-NMR: δ 201.0, 177.9, 163.6, 57.1, 47.2, 39.2, 31.8, 31.1, 30.2, 29.6, 29.4, 29.3, 29.1, 29.0, 28.4, 24.2, 22.9, 22.6, 21.1, 14.1.

3-[1-(2-Oxo-dodecanoyl)-pyrrolidin-2-yl]propionic Acid (OA37)

1H NMR: δ 4.21 (1H, m, CH), 3.54 (2H, m, CH$_2$NH), 2.84 (2H, m, CH$_2$COCO), 2.35 (2H, m, CH$_2$COOH), 2.01-1.41 (8H, m, 4×CH$_2$), 1.25 (14H, m, 7×CH$_2$), 0.86 (3H, t, J=7 Hz, CH$_3$). 13C-NMR: δ201.0, 177.6, 164.1, 57.1, 47.2, 39.3, 31.9, 31.2, 29.5, 29.4, 29.3, 29.1, 28.6, 24.2, 22.9, 22.6, 14.1.

5-octylcarbamoyloxy-4-(S)-(2-oxo-dodecanoylamino)-pentanoic Acid (OA16)

$[\alpha]_D$–16.8.8 (c 0.26 CHCl$_3$). 1H NMR: δ7.22 (1H, m, NHCO), 4.85 (1H, m, OCONH), 4.15 (3H, m, CH, CH$_2$OCONH), 3.15 (2H, m, NHCH$_2$), 2.91 (2H, t, J=7.8 Hz, COCOCH$_2$), 2.40 (2H, m, CH$_2$COOH), 1.90 (2H, m, CH$_2$), 1.70-1.40 (4H, m, 2×CH$_2$), 1.27 (24H, m, 12×CH$_2$), 0.89 (6H, t, J=6.8 Hz, 2×CH$_3$). 13C NMR: δ 198.9, 176.9, 160.2, 156.0, 65.5, 48.6, 41.2, 36.8, 31.9, 31.8, 30.3, 29.8, 29.5, 29.4, 29.3, 29.2, 29.0, 26.7, 26.3, 23.1, 22.6, 14.1.

5-ethylcarbamoyloxy-4-(S)-(2-oxo-dodecanoylamino)-pentanoic Acid (OA30)

$[\alpha]_D$–25.6 (c 1 CHCl$_3$). m.p. 70-720 C. 1H NMR: δ 7.25 (1H, m, NHCOCO), 4.85 (1H, m, OCONH, 4.15 (3H, m, CH$_2$OCONH, CH), 3.20 (2H, m, NHCH$_2$), 2.90 (2H, t, J=7.4 Hz, CH$_2$COCO), 2.42 (2H, m, CH$_2$COOH), 1.93 (2H, m, CH$_2$), 1.59 (2H, m, CH$_2$), 1.29 (14H, m, 7×CH$_2$), 1.14 (3H, t, J=7.4 Hz, NHCH$_2$CH$_3$), 0.88 (3H, t, J=7 Hz, CH$_3$). 13C NMR: δ 198.8, 177.3, 160.1, 156.0, 65.5, 48.4, 36.7, 35.9, 31.8, 30.3, 29.4, 29.3, 29.2, 29.0, 28.9, 26.2, 23.0, 22.6, 15.0, 14.1.

5-ethylcarbamoyloxy-4-(R)-(2-oxo-dodecanoylamino)-pentanoic Acid (OA32)

$[\alpha]_D$+26.1 (c 1 CHCl$_3$).m.p. 70-720 C. 1H NMR: δ7.25 (1H, m, NHCOCO), 4.82 (1H, m, OCONH), 4.19 (3H, m, CH$_2$OCONH, CH), 3.21 (2H, m, NHCH$_2$), 2.90 (2H, t, J=7.4 Hz, CH$_2$COCO), 2.42 (2H, m, CH$_2$COOH), 1.98 (2H, m, CH$_2$), 1.59 (2H, m, CH$_2$), 1.29 (14H, m, 7×CH$_2$), 1.14 (3H, t, J=7.4 Hz, NHCH$_2$CH$_3$), 0.88 (3H, t, J=7.0 Hz, CH$_3$). 13C NMR: δ 198.7, 177.0, 160.0, 155.9, 65.4, 48.4, 36.6, 35.8, 31.7, 30.2, 29.4, 29.2, 29.1, 28.9, 26.1, 22.9, 22.5, 15.0, 13.9.

4-Ethylcarbamoyl-4-(S)-(2-oxo-dodecanoylamino)-butyric Acid (OA29)

1H NMR: δ 8.10 (1H, d, J=9 Hz, NHCOCO), 7.20 (1H, m, CON), 4.65 (1H, m, CH), 3.30 (2H, m, NHCH$_2$), 2.87 (2H, t, J=7.4 Hz, CH$_2$COCO), 2.45 (2H, m, CH$_2$COOH), 2.11 (2H, m, CH$_2$), 1.57 (2H, m, CH$_2$), 1.25 (14H, m, 7×CH$_2$), 1.15 (3H, t, J=7.0 Hz, NHCH$_2$CH$_3$), 0.87 (3H, t, J=6.6 Hz, CH$_3$). 13C NMR: δ 198.0, 176.2, 170.6, 160.5, 52.1, 37.0, 34.7, 31.8, 29.8, 29.5, 29.4, 29.3, 29.2, 29.0, 27.5, 23.0, 22.6, 14.4, 14.1.

4-Ethylcarbamoyl-4-(R)-(2-oxo-dodecanoylamino)-butyric Acid (OA31)

$[\alpha]_D$+11.6 (c 0.5 CHCl$_3$).m.p. 109-1120 C. 1H NMR: δ 8.02 (1H, d, J=9 Hz, NHCOCO), 7.03 (1H, m, CONH), 4.63 (1H, m, CH), 3.32 (2H, m, NHCH$_2$), 2.89 (2H, t, J=7.4 Hz, CH$_2$COCO), 2.49 (2H, m, CH$_2$COOH), 2.12 (2H, m, CH$_2$), 1.59 (2H, m, CH$_2$), 1.23 (14H, m, 7×CH$_2$), 1.17 (3H, t, J=7.0 Hz, NHCH$_2$CH$_3$), 0.88 (3H, t, J=6.6 Hz, CH$_3$). 13C NMR: δ 197.9, 175.9, 170.1, 160.2, 52.0, 36.8, 34.5, 31.7, 29.7, 29.4, 29.3, 29.2, 29.1, 28.9, 27.6, 22.9, 22.5, 14.3, 14.0.

4-Decylcarbamoyl-4-(S)-(2-oxo-hexadecanoylamino)-butyric Acid (OA15)

$[\alpha]_D$–10.2 (c 0.5 CHCl$_3$). m.p. 91-930 C. 1H NMR: δ7.95 (1H, d, J=9.2 Hz, NHCOCO), 6.99 (1H, m, CONH), 4.66 (1H, m, CH), 3.25 (2H, m, NHCH$_2$), 2.87 (2H, t, J=7.2 Hz, CH$_2$COCO), 2.46 (2H, m, CH$_2$COOH), 2.10 (2H, m, CH$_2$), 1.54 (4H, m, 2×CH$_2$), 1.23 (36H, m, 18×CH$_2$), 0.88 (6H, t, J=6.6 Hz, 2×CH$_3$). 13C NMR: δ 197.8, 175.9, 170.2, 160.3, 52.1, 39.8, 37.1, 31.9, 29.6, 29.5, 29.4, 29.3, 29.0, 27.7, 26.8, 23.0, 22.7, 14.1.

2-(S)-(2-Oxo-dodecanoylamino)-pentanedioic Acid (OA33)

$[\alpha]_D$+24.4 (c 0.5 CHCl$_3$). m.p. 97-98° C. 1H NMR: δ 7.61 (1H, d, J=9.2 Hz, NHCOCO), 4.61 (1H, m, CH), 2.91 (2H, t, J=7.4 Hz, CH$_2$COCO), 2.54 (2H, m, CH$_2$COOH), 2.31 (2H, m, CH$_2$), 1.61 (2H, m, CH$_2$), 1.26 (14H, m, 7×CH$_2$), 0.88 (3H, t, J=6.6 Hz, CH$_3$). 13C NMR: δ 198.1, 178.7, 176.5, 159.8, 51.2, 36.7, 31.9, 29.5, 29.4, 29.3, 29.0, 26.1, 23.1, 22.7, 14.1.

4-(2-Oxo-6-phenyl-hexanoylamino)-butyric Acid (OA35)

m.p. 60-620 C. 1H NMR: δ7.27-7.15 (6H, m, C$_6$H$_5$, NHCOCO), 3.35 (2H, m, CH$_2$NH), 2.94 (2H, t, J=7.4 Hz, CH$_2$COCO), 2.60 (2H, m, CH$_2$), 2.38 (2H, m, CH$_2$), 1.86 (2H, m, CH$_2$), 1.64 (4H, m, 2×CH$_2$). 13C NMR: δ 198.8, 178.8, 160.3, 142.0, 128.3, 125.7, 38.6, 36.5, 31.4, 30.7, 24.2, 22.6.

4-(2-Oxo-5-phenyl-pentanoylamino)-butyric Acid (OA36)

m.p. 65-670 C. 1H NMR: δ7.25-7.11 (6H, m, C$_6$H$_5$, NHCOCO), 3.33 (2H, m, CH$_2$NH), 2.86 (2H, t, J=7.4 Hz, CH$_2$COCO), 2.60 (2H, m, CH$_2$), 2.36 (2H, m, CH$_2$), 1.86 (2H, m, CH$_2$), 1.64 (4H, m, 2×CH$_2$). 13C NMR: δ 198.8, 178.5, 160.3, 141.2, 128.4, 126.0, 38.5, 36.1, 34.9, 31.2, 24.7, 24.0.

4-[(2-oxooctanoyl)amino]butanoic Acid (OA28)

$^1$H NMR δ 7.22 (1H, m, NM, 3.38 (2H, m, CH$_2$NH), 2.91 (2H, t, J=7 Hz, CH$_2$CO), 2.39 (2H, t, J=7 Hz, CH$_2$COOH), 1.88 (2H, m, CH$_2$CH$_2$COOH), 1.58 (2H, m, CH$_2$CH$_2$CO), 1.25 (6H, m, 3 CH$_2$), 0.83 (3H, t, J=7 Hz, CH$_3$); $^{13}$C NMR δ 199.2, 178.4, 160.4, 38.5, 36.7, 31.5, 31.2, 28.6, 24.1, 22.4, 13.9

4-[(2-oxohexadecanoyl)amino]butanoic acid (OA1).

$^1$H NMR δ 7.20 (1H, m, NH), 3.36 (2H, m, CH$_2$NH), 2.90 (2H, t, J=7 Hz, CH$_2$CO), 2.39 (2H, t, J=7 Hz, CH$_2$COOH), 1.87 (2H, m, CH$_2$CH$_2$COOH), 1.56 (2H, m, CH$_2$CH$_2$CO), 1.25 (22H, m, 11 CH$_2$), 0.83 (3H, t, J=7 Hz, CH$_3$); $^{13}$C NMR δ 199.2, 178.3, 160.4, 38.5, 36.4, 31.9, 30.9, 29.6, 29.3, 29.0, 24.2, 22.6, 14.1.

(4S)-4-[(2-Oxododecanoyl)amino]octanoic acid. (OA4)

mp 50-52° C.; $[\alpha]_D$–1.8 (c 0.5 CHCl$_3$); MS (FAB): m/z (%): 378 (35) [m+Na$^+$], 356 (45) [m+H$^+$]; $^1$H NMR δ 6.86

(1H, d, J=9.4 Hz, NH), 3.90 (1H, m, CHNH), 2.90 (2H, t, J=7.8 Hz, CH$_2$COCO), 2.35 (2H, t, J=6.3 Hz, CH$_2$COOH), 2.01-1.05 (24H, m, 12CH$_2$), 0.87 (3H, t, J=6.0 Hz, CH$_3$); $^{13}$C NMR δ 199.4, 178.5, 160.1, 49.3, 36.8, 34.7, 31.8, 30.7, 29.8, 29.5, 29.4, 29.3, 29.2, 29.0, 27.9, 23.1, 22.6, 22.4, 14.1, 13.9.

(4R)-4-[(2-Oxododecanoyl)amino]octanoic acid ("OA7").

Spectroscopic data was identical to those obtained for the (S)-enantiomer.

D. Pharmaceutical PLA$_2$ Inhibitory Compositions and Use Thereof.

For use in therapeutic applications (e.g., treatment for pain, inflammation, or hyperalgesia), the particular amount of PLA$_2$ inhibitor to be delivered will depend on many factors, including the effect to be achieved, the type of organism to which the composition is delivered, delivery route, dosage regimen, and the age, health, and sex of the organism. As such, the particular dosage is left to the ordinarily skilled artisan's discretion.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual inhibitors, and can generally be estimated based on $X_I(50)$ found to be usually effective in in vitro and in vivo animal models (see, e.g., Example 7). In general, dosage is from 0.01 μg to 100 g per kg of body weight, and may be given once or more daily, weekly, monthly or yearly, as needed.

Toxicity is expected to be low or absent at clinically effective dosages of PLA$_2$ inhibitors of the invention. The data provided in the examples were obtained with no evidence of cytotoxicity in the ex vivo treated cells, or in animals treated in vivo. Further, gene-targeted mice who lack Group IVA PLA$_2$ altogether are much less prone to inflammatory pathological responses to disease, stresses, and physical injuries, which in essence protects them from cellular and systemic damage. These animals are fairly normal in all other respects suggesting that substantial inhibition of cPLA$_2$ activity should not have deleterious effects, especially over the course of relatively short-term treatments. Indeed, use of the PLA$_2$ inhibitors and methods of the invention to treat various inflammatory conditions should avoid many side effects and drawbacks of current therapies and treatments.

The PLA$_2$ inhibitors of the invention may be administered in any form including pharmaceutically acceptable salts, esters, or salts of such esters, or any other compound which, upon administration to an animal including a human, is capable of providing (directly or indirectly) the biologically active metabolite or residue thereof. The term "pharmaceutically acceptable salts" refers to physiologically and pharmaceutically acceptable salts of the compounds of the invention: i.e., salts that retain the desired biological activity of the parent compound and do not impart undesired toxicological effects thereto.

In addition, the invention encompasses administration of prodrug forms of PLA$_2$ inhibitors; i.e., those prepared in an inactive form that is converted to an active form (drug) within the body or cells thereof by the action of endogenous enzymes or other chemicals and/or conditions. Accordingly, the invention encompasses prodrugs and pharmaceutically acceptable salts of the PLA$_2$ inhibitors of the invention.

Pharmaceutically acceptable base addition salts are formed with metals or amines, such as alkali and alkaline earth metals or organic amines. Examples of metals used as cations are sodium, potassium, magnesium, calcium, and the like. Examples of pharmaceutically useful amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. Pharma Sci.* 66, 1-19 (1977)). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Neuraxial, e.g., intrathecal or intraventricular, routes of administration may be preferred for certain applications (e.g. hyperalgesia), whereas oral dosing may also be applicable and is preferred for other applications (e.g., peripheral inflammation and pain). Compositions and formulations for intrathecal or intraventricular administration may include sterile aqueous solutions, emulsions and liposome-based formulations, which may also contain buffers, diluents and other suitable additives such as, but not limited to, penetration enhancers, carrier compounds and other pharmaceutically acceptable carriers or excipients.

The compositions of the present invention can comprise the usual non-toxic, pharmaceutically acceptable carriers for solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

There are many enzymes and proteins that are homologous to cPLA$_2$ whose functions are less well known, such as GVI PLA$_2$, GIVB and GIVC. The common catalytic mechanism and divergent sequence homology of these enzymes makes them attractive co-targets along with cPLA$_2$. For example, inhibitors active against PLA$_2$ homologs which share a Ser-Asp active site with cPLA$_2$ and iPLA$_2$ may be co-administered with the PLA$_2$ inhibitors of the invention. Specific inhibition targets may, therefore, include Group IVB PLA$_2$, Group IVC PLA$_2$, Group VIA PLA$_2$, Group VIB PLA$_2$, neuropathy target esterase, phospholipase B (PLB's) from fungi, patatins in plants and various bacterial homologs such as ExoU from *Pseudomonas aeruginosa* (Phillips, R. M., Six, D. A., Dennis, E. A., and Ghosh, P., manuscript in preparation). The PLB's have been found to be critical for pathogenicity of fungi such as *Candida albicans*, and ExoU has also been found to be critical for cytotoxicity of a large percent of opportunistic *Pseudomonas auruginosa*.

Such homologs have various substrates, ranging from phospholipids to lysophospholipids to other ester-containing compounds. All, however, are related to cPLA$_2$ and to one another in their identical catalytic residues and catalytic mechanism. The invention therefore further encompasses co-administration of, or concurrent treatment with, inhibitors of $PLA_2$ homologs.

Data demonstrating the efficacy of the methods and compositions of the invention are provided in the Examples below. The examples shall not be construed as limiting the scope of the invention, which is defined by the appended claims. Abbreviations used in the Examples, such as "h" for hours, shall have their ordinary meanings.

The invention having been fully described, it will be readily apparent to those skilled in the relevant arts that other suitable modifications and adaptations to the methods and applications described herein may be made without departing from the scope of the invention or any embodiment thereof. It will therefore be understood that following examples are included herewith for purposes of illustration only and are not intended to be limiting of the invention.

EXAMPLE 1

General Methodology Utilized for Ex Vivo Experiments

Animals: Experiments were carried out according to protocols approved by the Institutional Animal Care Committee of University of California, San Diego. Male Holtzman Sprague-Dawley rats (250-350 g; Harlan Industries) were housed pair-wise in cages and maintained on a 12-hr light/dark cycle with free access to food and water at all times.

Intrathecal catheter implantation: For intrathecal drug delivery, chronic lumbar catheters were implanted in rats under isoflurane anesthesia according to a modification of the procedure described by Yaksh (Yaksh and Rudy, 1976). A polyethylene catheter (PE-10) was inserted through an incision in the atlanto-occipital membrane and advanced caudally to the rostral edge of the lumbar enlargement. Studies involving rats with chronic IT catheters were carried out 5 days after implantation, and rats were housed individually after implantation under the same conditions described above. Exclusion criteria were i) presence of any neurological sequel ii) 20% weight loss after implantation or iii) catheter occlusion.

Induction of inflammation and assessment of hyperalgesia: To induce a state of local inflammation, 2 mg of carrageenan (Sigma, St. Louis, Mo.; 100 μl of 20% solution (w/v) in physiological saline) was injected subcutaneously into the plantar surface of the left hind paw. To assess the thermally evoked paw-withdrawal response, a commercially available device was used, consisting of a glass surface (maintained at 25° C.) on which the rats were placed individually in Plexiglas cubicles (9×22×25 cm). The thermal nociceptive stimulus originates from a focused projection bulb positioned below the glass surface. The stimulus is delivered separately to either hind paw of each test subject with the aid of an angled mirror mounted on the stimulus source. A timer is actuated with the light source, and latency was defined as the time required for the paw to show a brisk withdrawal as detected by photodiode motion sensors that stopped the timer and terminated the stimulus.

Basal paw withdrawal latencies (PWL) were assessed at time (T)=−15 min. At T=−10 min the animals received intrathecal vehicle or drug and at T=0 the carrageenan was injected IPLT. Withdrawal latencies were then assessed at T+30, 60, 90, 120, 150, 180 and 240 min and expressed as the mean PWL of the left and right paws at each time point. The data was also presented as hyperalgesic index (HI). Hyperalgesic index is the percentage change from baseline averaged over each of the time points for the respective models. These values were cumulated [that is, the sum of (base line−post-drug latency)/(base line) divided by the number of measurements] so that increasing values indicate increasing hyperalgesia.

Formalin induced flinching. Flinching was assessed by an automated detection system. Using the system, a soft metal band (10 mm wide and 27 mm long, shaped into a C, and weighing ~0.5 g) is placed on the hind paw of the animal being tested. The open part of the C is positioned at the top of the paw with the arms of the C gently compressed to form a bracelet around the paw. Animals are allowed to acclimate in individual Plexiglas chambers for 1 h before being moved to a test chamber. Just before the animal's placement into the test chamber, it is briefly restrained in a cloth towel, and 5% formalin (in volumes of 50 μl physiological saline) is injected into the dorsal side of the banded paw. Data collection is initiated after the animal is placed inside the test chamber.

Pain behavior was quantified by counting the incidences of spontaneous flinching or shaking of the injected paw. The flinches were counted for 1-min. periods for 60 minutes. Two phases of spontaneous flinching of the injected paw were observed after formalin injection and defined as phase 1 (0-9 min.) and phase 2 (10-60 min.). Upon completion of the 60-min observation, the rat was killed with pentobarbital sodium phenytoin sodium solution.

Drugs and Delivery. To examine the effects of drugs on carrageenan induced hyperalgesia and flinching behavior, rats received intrathecal or intraperitoneal injections of the drug. Intrathecal injections were done in rats that had been previously implanted with chronic intrathecal catheters (see above) using drug volumes of 10 μl followed by a 10-μl flush using vehicle. Intraperitoneal drugs were delivered in volumes of 0.5 ml/kg. AATFMK, MAFP and BEL (Cayman Chemical) were dissolved in DMSO (Sigma). The highest soluble dose was tested in regard to side effects in a pilot dose range study. The vehicle per se gave rise to an initial injection reaction in the form of scratching and vocalization that lasted for approximately 10 seconds. The drugs were well tolerated up to the highest soluble dose. No effect on normal behavior was observed except for BEL.

Tissue Preparation: Prior to sacrifice the rats were deeply anesthetized and after decapitation the spinal cords were ejected from the spinal column by a saline-filled syringe. The lumbar part of the spinal cord was frozen on dry ice and stored at −70° C. Frozen spinal cords were pulverized using a BioPulverizor (Biospec Products) pre-chilled on dry ice. Pulverized tissue was then transferred to a microcentrifuge tube and mixed with 750 μL lysis buffer: 10 mM Hepes, pH 7.5, 1 mM EDTA, 0.34M sucrose. 20 μL mammalian protease inhibitor cocktail (Sigma) was added immediately. Samples were vortexed and sonicated until homogenous and then centrifuged at 16,000×g, 4° C., 40 minutes. Supernatants were transferred to a fresh eppendorf tube and the pellet was discarded.

Western Blot: The protein concentration of the supernatant was determined by Bradford assay using BSA as the standard. 30 μg protein was run on a NuPAGE 4-12% Bis-Tris gel (Invitrogen) and then transferred to nitrocellulose. Protein was detected using an anti-human $iPLA_2$ antibody (a gift from Genetics Institute).

cDNA preparation: mRNA was extracted from supernatants using the TRIzol method (Gibco BRL) and contaminating DNA was eliminated by DNA-free treatment (Ambion) following the manufacturer's instructions. The concentration of the resulting DNA-free RNA was determined spectrophotometrically. cDNA was prepared using M-MLV reverse transcriptase (Gibco BRL) and oligo dT as the primer. Following cDNA preparation the samples were incubated with RNase H for 20 minutes at 37° C. to remove RNA.

$PLA_2$ gene fragment cloning: $PLA_2$ gene fragments were generated by PCR using the primers listed in the table below. The resulting fragments were purified from an agarose gel and cloned into the TOPO vector (Invitrogen). Each vector was sequenced to verify the identity of the insert and vector concentration was determined spectrophotometrically.

Q-PCR: Gene specific primers were designed using the Primer3 program (http://www-genome.wi.mit.edu/cgi-bin/primer/primer3.cgi/) or Primer Express 1.0 (Applied Biosystems). SYBR green was used to generate fluorescence for all genes tested except $PLA_2$ Groups IIA and V for which FAM probes were necessary to generate a single amplicon. Primer concentration and PCR conditions were optimized as described in the Applied Biosystems user bulletin and are listed below. Standard thermocycling conditions were used: 2 minutes at 50° C. UNG activation (for taqman chemistry), 10 minutes at 95° C. for polymerase activation, 40 cycles of 15 seconds at 95° C. and 1 minute at 60° C. Q-PCR results were analyzed by the standard curve method using untreated rat spinal cord to generate the standard curve. In the case of absolute quantification TOPO vector (Invitrogen) containing $PLA_2$ gene fragment inserts were used to generate the standard curve.

10 ng total cDNA was analyzed for each rat sample. GAPDH was used as the internal standard and acts as a loading control. Dissociation curves were generated following each Q-PCR run to verify the amplification of a single amplicon as is reccomended by Applied Biosystems. In the case of IIA and V where probes were utilized the PCR products were analyzed by agarose gel to verify the production of a single amplicon. PCR products were purified from gels and sequenced to confirm their identity. Primers, probes and PCR conditions are listed in the table below. Primer and probe concentrations listed are the final concentrations in the assay.

| Gene | Primer or Probe | Sequence | [Primer] or [Probe] (nM) |
|---|---|---|---|
| IB | F Primer | CTCCAAGGTCCCCTACAACA | 500 |
|  | R Primer | GAAGTGGGGTGACAGCCTAA | 500 |
| IIA | F Primer | TGAACAAGAAGCCATACCACCAT | 900 |
|  | R Primer | AGGAGGACCTTCATGCTGTCA | 900 |
|  | Probe | CCCATCCAAGAGAGC | 250 |
| IIC | F Primer | CTCCACCCTACCCAGGTACA | 500 |
|  | R Primer | AGCCTCTGGCATTGGTAGAA | 500 |
| IVA | F Primer | GACTTTTCTGCAAGGCCAAG | 300 |
|  | R Primer | CTTCAATCCTTCCCGATCAA | 300 |
| V | F Primer | CCATCCGGACCCAGTCCTAT | 300 |
|  | R Primer | CTTCCGGTCACAAGCACAAA | 300 |
|  | Probe | TGCGAACACGACTCCTTCTGTCCAG | 250 |
| VI | F Primer | GCCTTCGCAGGTATCAAAAG | 500 |
|  | R Primer | GGGAATCTGGTGAAAGTCCA | 500 |
| GAPDH | F Primer | ATGACTCTACCCACGGCAAG | 300 |
|  | R Primer | GATCTCGCTCCTGGAAGATG | 300 |

$PLA_2$ Activity Assays: Following homoginization and centrifugation, the spinal cord supernatants were assayed for $cPLA_2$ or $iPLA_2$ activity using the group specific assays developed in our laboratory (Yang et al., *Biochem;* 269: 278-288, 1999). Briefly the $cPLA_2$ assay conditions were: 100 µM lipid $PAPC/PIP_2$ (97/3) doping with 1% $^{14}C$ labeled PAPC in 400 µM triton X-100 mixed micelles, 100 mM Hepes, pH 7.5, 0.08 mM $CaCl_2$, 0.1 mg/ml BSA and 2 mM DTT. $iPLA_2$ assay conditions were: 100 µM DPPC doping with 1% $^{14}C$ labeled DPPC in 400 µM triton X-100 mixed micelles, 100 mM Hepes, pH 7.5, 5 mM EDTA, and 1 mM ATP. The total volume for each assay is 500 µL: 200 µL lipid, 250 µL assay buffer, 50 µL sample. In each case the amount of calcium or EDTA added was adjusted to account for the addition of EDTA in the lysis buffer to give the final concentrations listed above.

Lipid preparation: Lipid was dried under $N_2$ and lyopholized for at least one hour to remove all traces of chloroform. Lipid was then resuspended in 100 nM HEPES and triton X-100 and micelles were created by repeated vortexing and heating in hot water until the solution clarified. Samples were incubated with substrate for one hour at 40° C. The assay was then terminated and fatty acid extracted by the modified Dole assay. The amount of radioactive fatty acid released in the assay was determined by scintillation counting. Following analysis the data for the $cPLA_2$ assay was adjusted for contaminating $iPLA_2$ activity as described by Yang, et al. (Yang, et al., *Anal. Biochem.* 269: 278-288 (1999).

For the inhibitor studies the same phospholipid and buffer conditions were used as above with the addition of 4 µM or 0.8 mole % inhibitor. All commercial inhibitors were purchased from Cayman Chemical and their effectiveness was verified using pure GIVA or cell lysates known to contain $iPLA_2$ activity prior to assaying inhibitory effect in spinal homogenates. AAFTMK was incubated with homogenate for 4 hours prior to assay. MAFP and BEL were aliquoted into the lipid substrate immediately before the start of the assay.

Statistics Six to eight rats were included in each group for the formalin and carrageenan hyperalgesic measurements. Each timepoint and bar represents mean±SEM. Differences between groups were compared with one-way ANOVA using Statview statistical software. Three rats were included for each activity assay and PCR experiment. P-values were determined for the inhibitor assays using Graph Pad's on-line calculator.

EXAMPLE 2

Intrathecal $PLA_2$ Inhibitors Prevented Carrageenan-Induced Thermal Hyperalgesia Carrageenan induces a characteristic inflammation and associated thermal hyperalgesia. Baseline latencies were assessed for all animals before injection of carrageenan and the average time to response was 11.1±0.4 seconds for the left hind paw (ipsilateral) and 10.6±0.7 seconds for the right hind paw (contralateral). After carrageenan injection into the plantar side of the left hind paw a reduction in time to paw withdrawal was detected. The withdrawal latency time decreased to 3.2±0.7 seconds at 120 minutes after carrageenan injection (FIG. 1A). There was no change of withdrawal time for either of the two control groups receiving IT saline or IT vehicle (data not shown). Pre-treatment with either IT AATFMK or IT MAFP resulted in a potent dose-dependent prevention of carrageenan-induced thermal hyperalgesia (FIGS. 1A and C).

Importantly, there were no changes in the response latency of the uninflamed paw even at the highest doses of either drug. A statistically significant reduction in the hyperalgesic index occurred upon administration of 200 µg IT AAFTMK (26±13) or 300/µg IT MAFP (25±11) in comparison with rats that received vehicle control (77±4) (FIGS. 1B and D). Because of limitations in solubility, the maximum dose given intrathecally differs between the two compounds.

Figure 2:
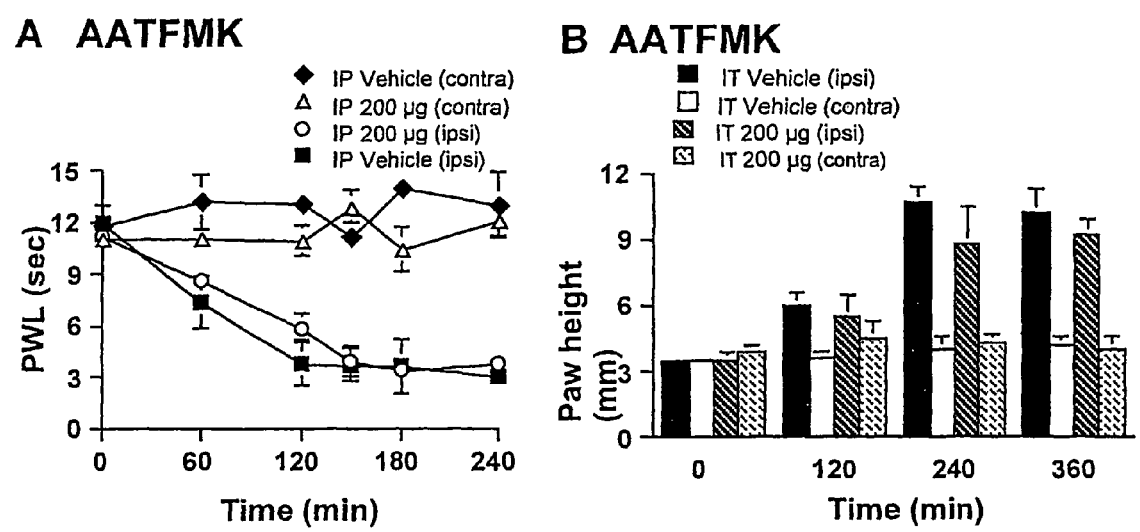
FIG. 2A) Thermal escape latency (PWL) plotted versus time after injection of carrageenan into plantar face of left hind paw of rats pretreated (−10 min) with intraperitoneal AATFMK (200 μg/0.5 ml, contralateral paw, open triangle; ipsilateral paw, open circles) or vehicle (contralateral paw, closed diamond; ipsilateral paw, closed square). B) Paw height of carrageenan injected (ipsi) and non-treated (contra) hind paws measured at different time points. The control group received IT vehicle and the other group received IT AATFMK (200 μg) ten minutes prior to carrageenan injection. Each time point and bar represent the average and SEM for 4-6 rats.

There was a brief period of vocalization and scratching, approximately 10 seconds, following IT injection of the vehicle or the $PLA_2$ inhibitors. A test of spontaneous movement indicated that the compounds had no apparent effect on normal motor function (Table 1) although a third, $iPLA_2$ specific inhibitor (bromoenol lactone) did have such an effect as discussed in Example 4. To confirm that the antihyperalgesic effect of the intrathecally delivered $PLA_2$ inhibitors was due to spinal actions and not peripheral actions following redistribution from spinal to peripheral sites, the same amount of AATFMK (200 μg) that was given intrathecally was given intraperitoneally (IP). As shown in FIG. 2A no effect on the carrageenan-induced thermal hyperalgesia was seen following IP administration of 200 μg AAFTMK when compared to the control group that received IP vehicle.

Additionally the effect of intrathecal injection of AATFMK on carrageenan induced paw edema was assessed by measurement of paw height. The height of the ipsilateral paw increased significantly over the course of the experiment. The paw height peaked at 6 hours (FIG. 2B) and was back at baseline after 72 hours (data not shown). The contralateral paw did not show any signs of height increase and the $PLA_2$ inhibitor treatment did not have a statistically significant effect on the height of the carrageenan injected paw (FIG. 2B).

Figure 3:
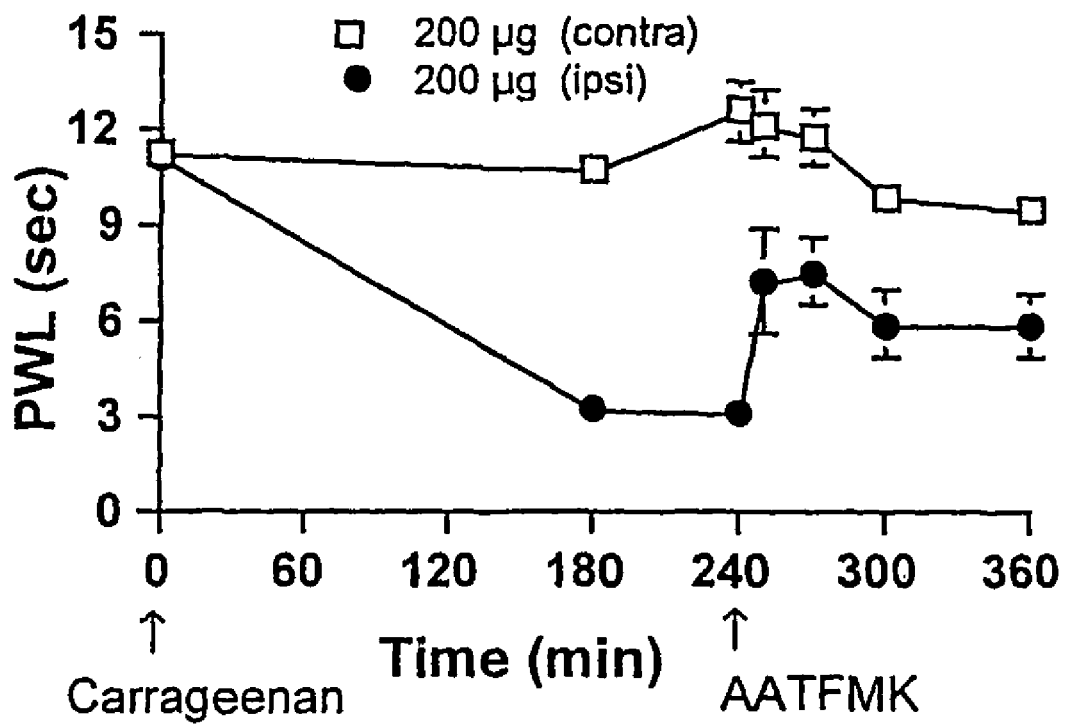
FIG. 3. Thermal escape latency (PWL) plotted versus time after injection of carrageenan into plantar face of left hind paw of rats posttreated (+180 mm) with IT AATFMK (200 μg) contralateral paw, open square; ipsilateral paw, closed circles. Each time point represents the average and SEM for 4-6 rats.

In order to examine the effect of the $PLA_2$ inhibitors on a state where thermal hyperalgesia is already established, AAFTMK was administered intrathecally 180 minutes after the carrageenan injection into the paw. In this study it was noted that, in comparison to pretreatment that fully prevented the onset on thermal hyperalgesia, posttreatment only partially reversed the hyperalgesia (FIG. 3).

To evaluate the anti-inflammatory activity of 2-oxoamide inhibitors, the rat carrageenan-induced paw edema assay was employed as a model for acute inflammation (reference drug indomethacin, 47% inhibition at 0.011 mmol/kg). The experiments were conducted on Fisher 344 female rats weighing 200-260 g. Acute anti-inflammatory activity was measured after 3.5 h by reduction of rat paw carrageenan edema, induced by injection of 0.1 mL carrageenan 2% (K100, commercially available) in sterilized saline intradermally into the right footpad. The examined compounds were administered intraperitoneally (ip) simultaneously. Control animals accepted only vehicle.

The acetic acid writhing test was used to assess the analgesic activity in rats (reference drug sodium acetylsalicylate, at 1 mmol/kg, 93.4%). The inhibitors were given ip and 30 min later 1 mL/100 g body weight of 0.6% acetic acid was given ip. After 5 min, the number of stretches were counted each 5 min for a period of 30 min. The total number of writhes exhibited by each animal in the group was recorded and compared to that of the vehicle treated control group.

The $ED_{50}$ values for 4-(2-oxohexadecanoylamino)-butyric acid (OA1) and (4S)-4-(2-oxododecanoylamino)-octanoic acid (OA4) were 0.01 mmol/kg and 0.1 mmol/kg, respectively. At a dose of 0.01 mmol/kg, corresponding to the $ED_{50}$ dose of the carrageenin paw edema test, 4-(2-oxohexadecanoylamino)-butyric acid (OA1) exhibited 92.7% analgesic activity. At a dose of 0.1 mmol/kg, corresponding to the $ED_{50}$ dose of the carrageenin paw edema test, (4S)-4-(2-oxododecanoylamino)-octanoic acid (OA4) exhibited 63% analgesic activity.

EXAMPLE 3

It Administration of $PLA_2$ Inhibitors Suppressed Formalin-Induced Flinching

Figure 4:
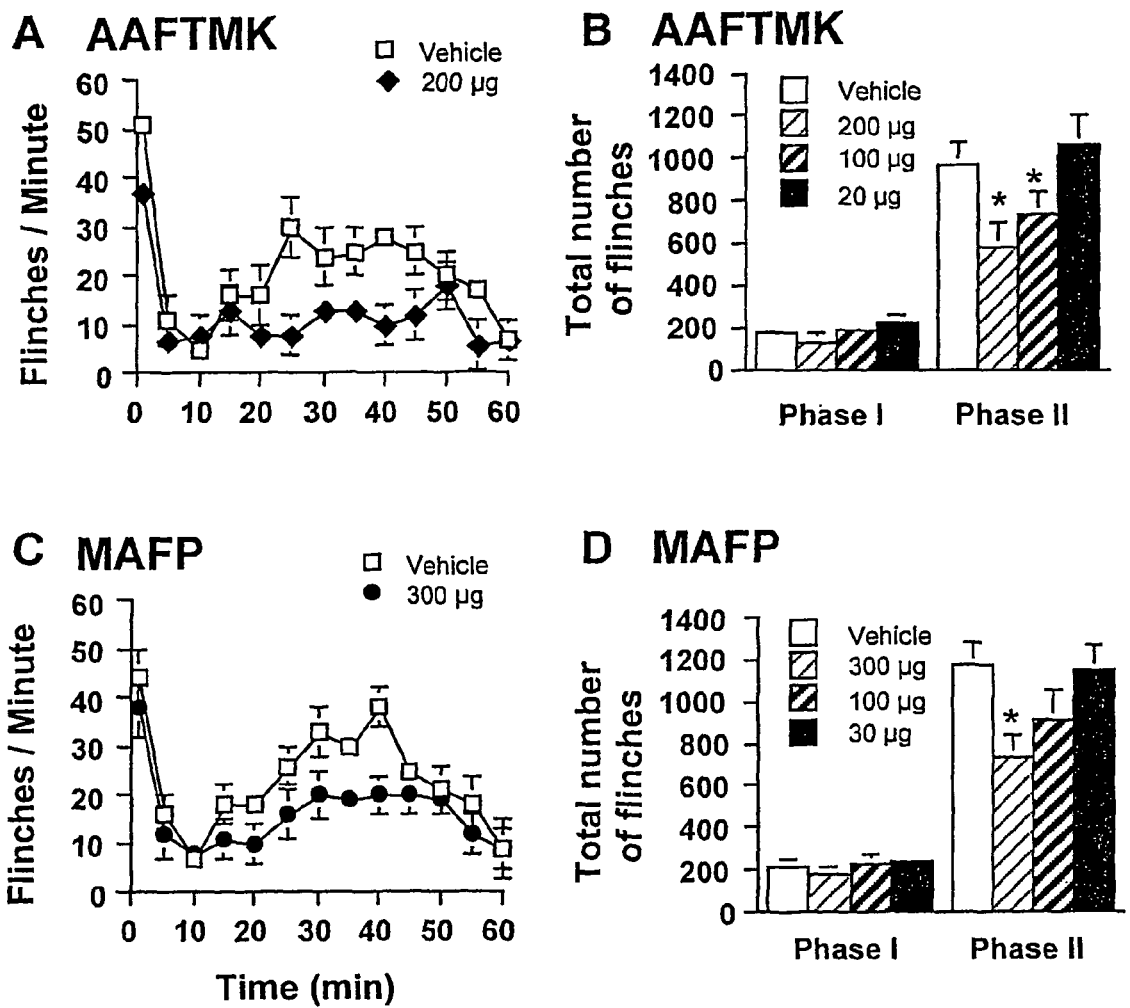
FIG. 4. Flinching behavior plotted versus time following injection of formalin into the dorsal side of the right hindpaw of rats pretreated (−10 mm) with IT vehicle (open squares) or A: IT AATFMK (200 µg; closed diamonds), or C: IT MAFP (300 µg; closed circle). Cumulative number of flinches during Phase 2 (10-60 mm, total number) observed after different doses of B: IT AATFMK and D: IT MAFP. Each timepoint and bar represents the average and SEM for 4-6 rats and (*) represents P<0.05 versus vehicle treated formalin injected group.

Injection of formalin into the dorsal side of the right hind paw evokes an initial burst of afferent input followed by a persistent low level discharge. This model predicts a biphasic increase in the activity of dorsal horn wide dynamic range neurons (Haley et al., *Brain Res.*, 518218-226 (1990)) and a parallel biphasic appearance of flinching (FIG. 4) (Yaksh, et al., *J. Appl. Physiol.*, 90: 2386-2402 (2001)). Pretreatment with AAFTMK and MAFP resulted in a dose-dependent reduction of the formalin induced flinching (FIGS. 4A, B and C). While Phase 1 was not significantly affected by the drugs, a statistically significant reduction was seen in Phase 2 (FIG. 4D) when compared to the group that received IT vehicle.

EXAMPLE 4

Intrathecal Injection of BEL, But not AATFMK and MAFP, Reduced Spontaneous Movement In order to investigate the effect of the intrathecally administrated $PLA_2$ inhibitors on spontaneous movement the rats were placed on the flinch-counting device without receiving a paw formalin injection. The vehicle showed a tendency to reduce the number of counts although it did not meet statistical significance (Table 1, supra). The total number of counts generated over 60 minutes starting 10 minutes after IT injection of AATFMK or MAPF showed no statistically significant difference in comparison to the vehicle treated group. IT injection of BEL however, resulted in a measurable reduction of spontaneous movement (212±32 counts compared to 306±36 counts after vehicle injection) (Table 1, supra).

IT injection of BEL 10 minutes prior to paw formalin treatment resulted in suppression of formalin induced flinching (data not shown) but because of the reduction of spontaneous movement it is not possible to determine whether this effect is due to an antihyperalgesic effect or sedation/motor dysfunction. The effect of intrathecal BEL on hyperalgesic conditions was not further studied.

EXAMPLE 5

RNA Message for $PLA_2$ Groups IB, IIA, IIC, IVA, V and VI is Present in the Spinal Cord But is not Upregulated Following Injury To determine the presence or absence of $PLA_2$ message in the spinal cord sequence specific primers were chosen to surround a splice junction for each rat $PLA_2$ gene available in the public database and RT-PCR was performed. Resulting fragments were then purified and sequenced to verify their identity. All $PLA_2$'s with sequences available in the public database were found to be present in the spinal cord with the exception of one (Group X).

To test for a possible upregulation in $PLA_2$ message following exposure to carrageenan, quantitative PCR (Q-PCR) was performed utilizing the primers used above. mRNA was extracted from non-treated rats or from rats either 2 hours or 4 hours following hind paw injection with carrageenan. cDNA was then made from the extracted mRNA. Changes in gene expression level were determined by Q-PCR using the standard curve method. Standard curves were constructed using cDNA from one of the control rats. GAPDH levels were determined by the same method and used as the internal reference.

Figure 5:
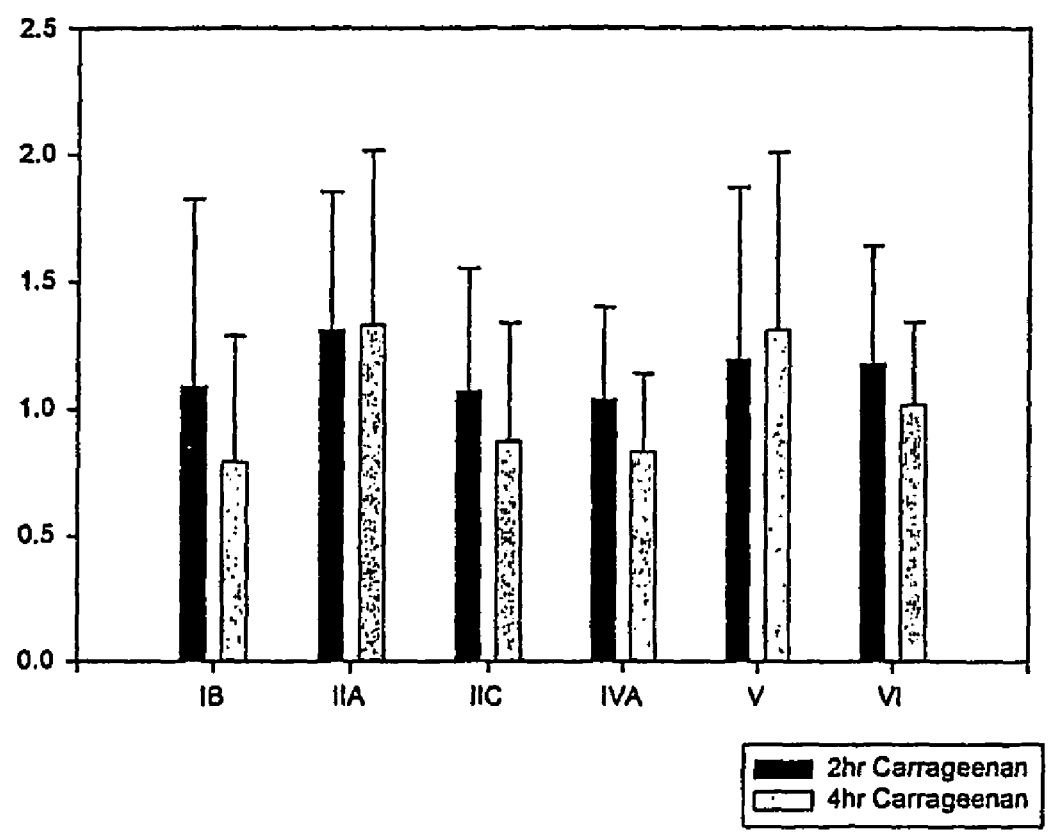
FIG. 5. Q-PCR analysis. A) Expression levels are determined by standard curve method. For each gene expression in control rat spinal cord is compared to expression in spinal cord of rats treated with carrageenan hind paw injection either 2 or 4 hours after injection.

Analysis by absolute quantitation (discussed below) indicated that no significant change in GAPDH levels occurred between control and treated animals. Following amplification, dissociation curves were generated or agarose gels were run for every sample to ensure specific amplification of a single amplicon. Analysis indicated that no upregulation of any of the $PLA_2$ genes following carrageenan injection occurred, as compared with control rats (FIG. 5).

Figure 6:
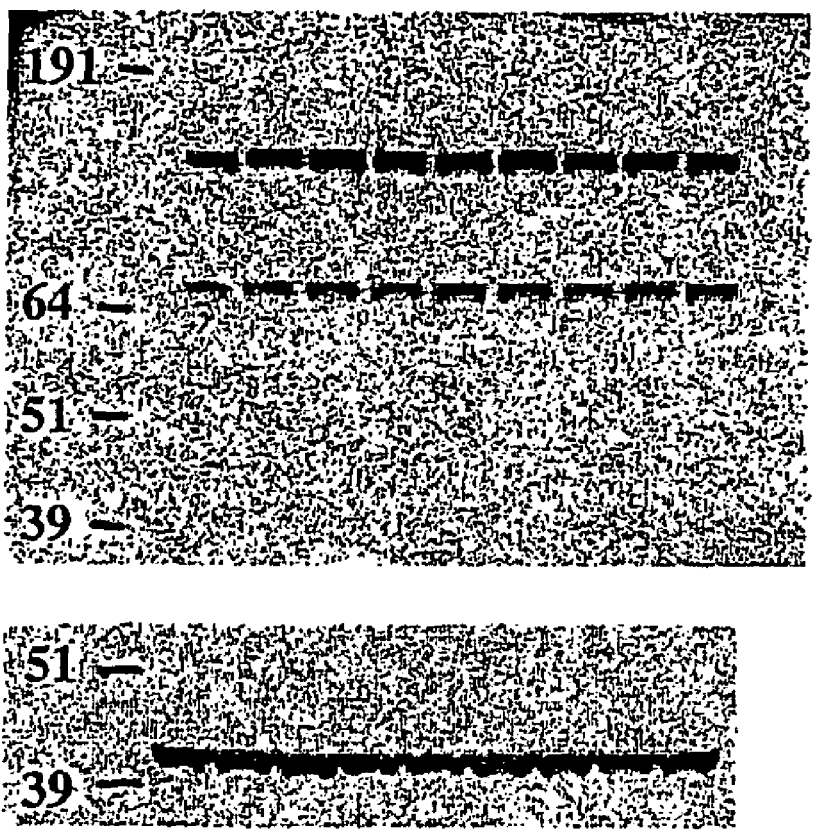
FIG. 6. iPLA$_2$ protein is expressed in rat lumbar spinal cord. Top: anti-human iPLA$_2$ antibody, Bottom: β-clin loading control. Lane (1) ladder, (2-4) control rat, (5-7) 2 hr carrageenan, (8-10) 4 hr carrageenan. No significant increase in activity was observed following carrageenan injection to the hind paw 120 minutes or 240 minutes after injection in comparison with control (0 minutes). Each value is the average of three rats assayed in duplicate.

Analysis by western blot also indicated that a stable level of $iPLA_2$ was maintained in control versus treated animals (FIG. 6). $iPLA_2$ has been reported to run at 60-65 kDa on SDS-PAGE. The larger band observed in FIG. 6 is likely dimerized enzyme as $IPLA_2$ is known to form oligomers through binding of its ankirin repeats.

The relative expression levels of the six $PLA_2$ genes were determined using the absolute quantitation method of Q-PCR. The gene fragments generated by PCR were cloned into the TOPO vector. The resulting circular DNA was then be quantitated by spectrophotometry and the copy number determined. These vectors were then serially diluted to have between 10,000 and 10 copies and Q-PCR was again performed on control rat samples using these vectors to generate the standard curves. Using this approach, it was confirmed that $PLA_2$ Groups IVA and VI are the predominant $PLA_2$ messages found in rat spinal cord.

EXAMPLE 6

Both $cPLA_2$ and $iPLA_2$ are Active in the Spinal Cord

Figure 7:
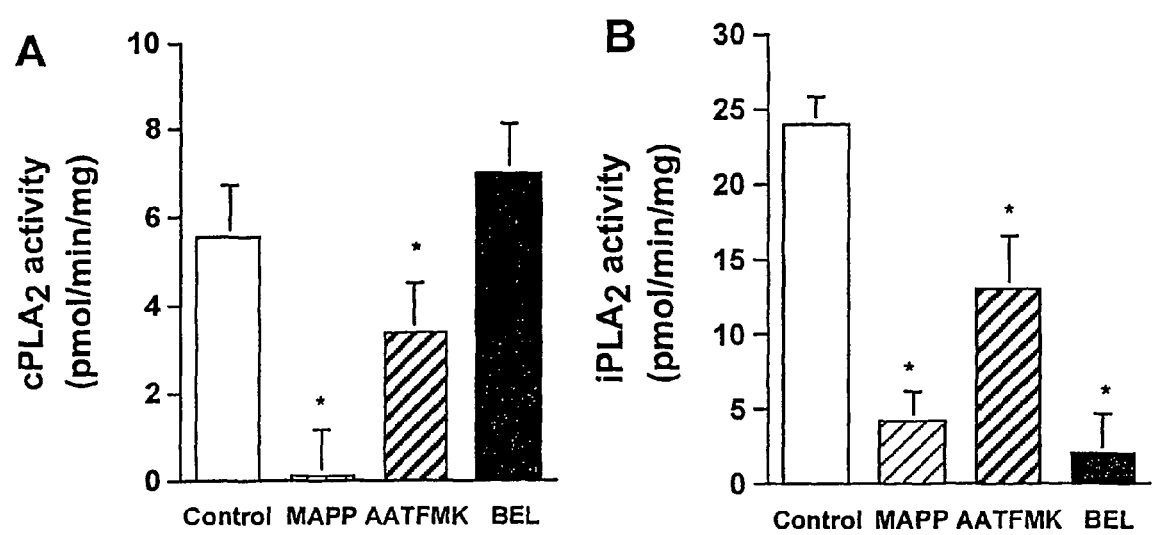
FIG. 7. Inhibition of spinal iPLA$_2$ activity in vitro. Rat lumbar spinal cord homogenates were assayed for A: cPLA$_2$ activity, or B: iPLA$_2$ activity for one hour in the presence of 0.8 mole % inhibitor. Each value is the average of three rats assayed in duplicate. *P-values are all less than 0.009.
Figure 8:
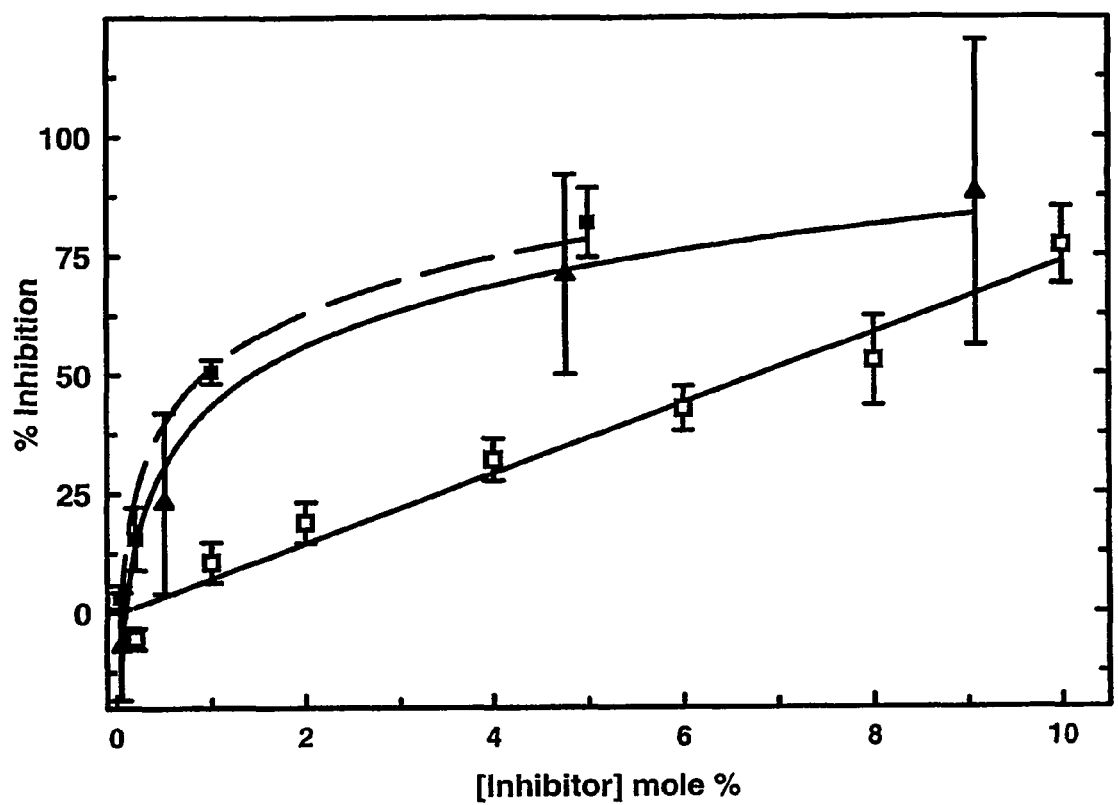
FIG. 8. The activity of cPLA$_2$ was tested on mixed micelles composed of TX-100 (400 AK, 1-palmitoyl-2-(1-[$^{14}$C])-arachidonoyl PC (97 µM, 100,000 cpm) and PIP$_2$ (3 µM, 0.6 mole %). The surface concentration of various inhibitors in the mixed micelles was increased as shown for OA1 (▲), OA4 (■), and OA7 (□). The data for OA1 and OA4 were fit to a simple logarithmic function (OA1, solid curve and OA4, dashed curve). The X$_f$(50) determined by this fit was 0.017±0.009 for OA1 and 0.009±0.004 for OA4. The data for OA7 were fit to a linear function. The X$_f$(50) for OA7 determined by this fit was 0.068±0.005.
Figure 9:
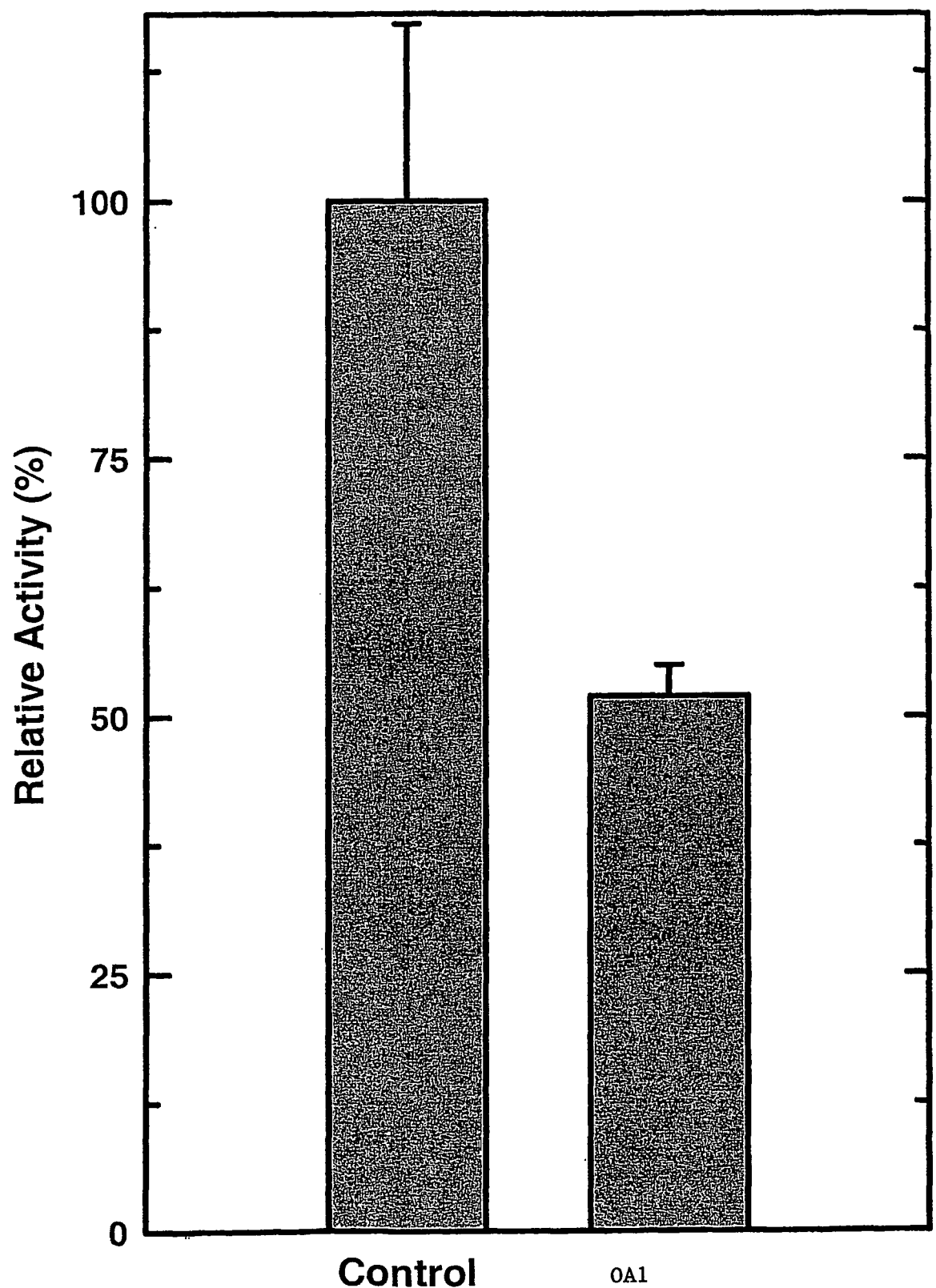
FIG. 9. The relative activity of cPLA$_2$ was tested on mixed micelles composed of TX-100 (3 mM) and 1-palmitoyl-2-(1-[$^{14}$C])-arachidonoyl PC (1 mM, 200,000 cpm) with no PIP$_2$ present. The surface concentration of OA1 was 0 mole fraction (left bar) and 0.01 mole fraction (40 µM, right bar). The data for both bars have been normalized to the control (left bar).
Figure 10:
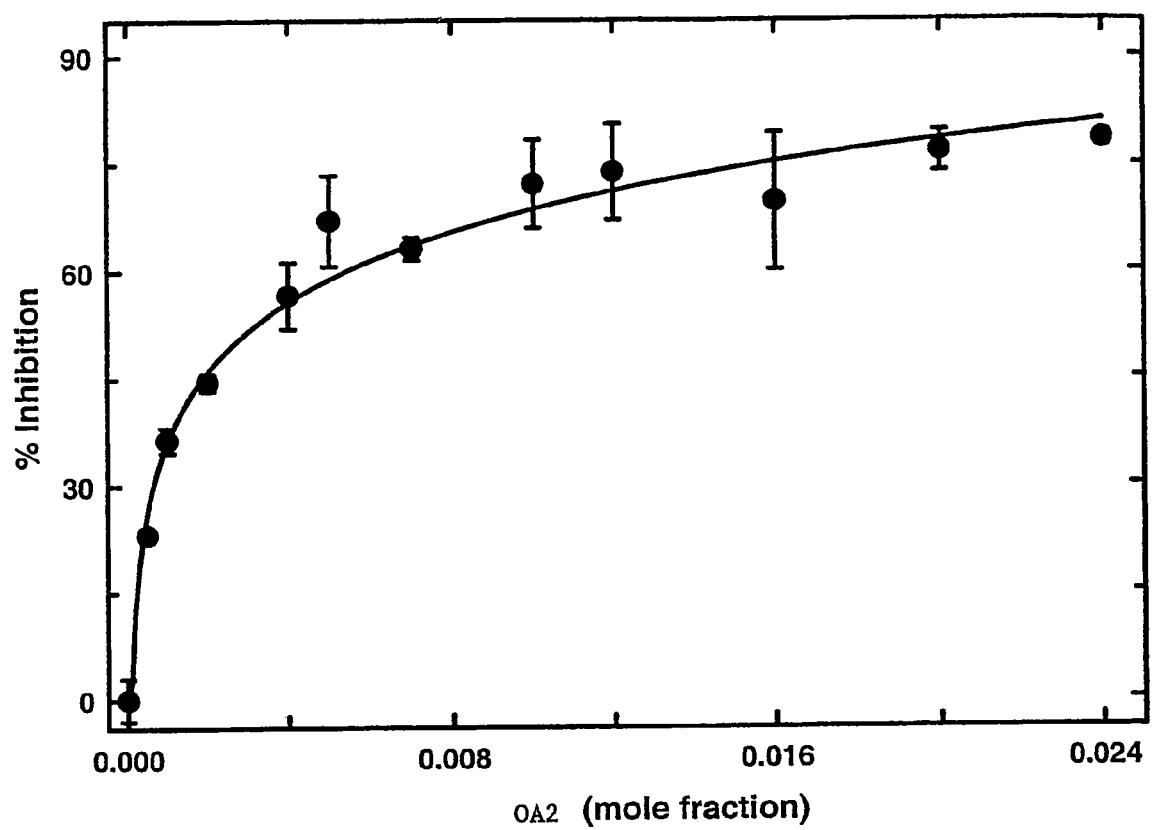
FIG. 10. The activity of cPLA$_2$ was tested on mixed micelles composed of TX-100 (3 mM) and 1-palmitoyl-2-(1-[$^{14}$C])-arachidonoyl PC (1 mM, 200,000 cpm) with no PIP$_2$ present. The surface concentration of OA4 was increased as shown. The curve is a fit of the data to a simple log function. The curve values give an X$_f$(50) of 0.0027±0.0012 mole fraction.
Figure 11:
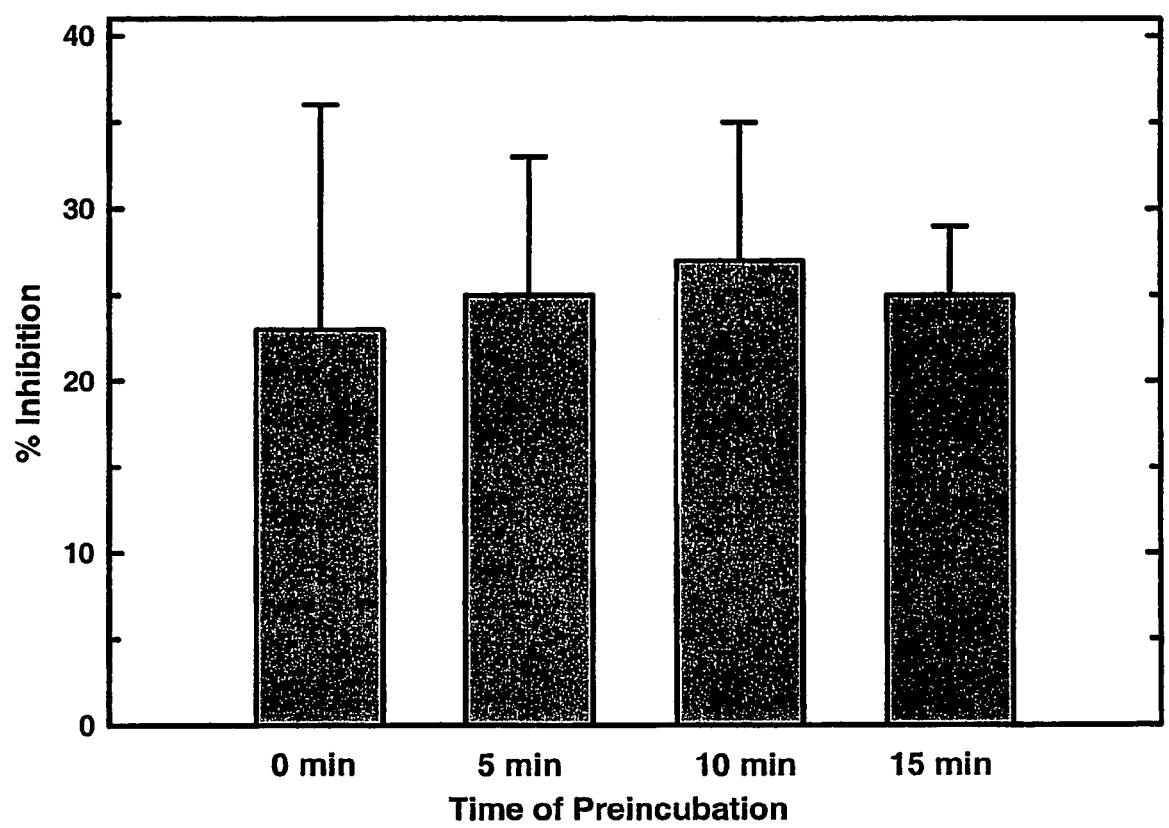
FIG. 11. The activity of cPLA$_2$ was tested on mixed micelles composed of TX-100 (400 AK, 1-palmitoyl-2-(1-[$^{14}$C])-arachidonoyl PC (97 µM, 100,000 cpm) and PIP$_2$ (3 µM, 0.6 mole %). The micelles also contained a final concentration of 0.005 mole fraction of OA1 (20 µM). cPLA$_2$ was first preincubated with OA1 for the indicated times (at 200 µM) before 10-fold dilution of the enzyme and inhibitor into the substrate-containing solution.

Having found evidence for $PLA_2$ message and protein, the spinal cord was next tested for $PLA_2$ activity. Again analysis was performed on non-treated rats or carrageenan-treated rats either 2 hours or 4 hours following hind paw injection. Both $cPLA_2$ and $iPLA_2$ show significant activity in the spinal cord homogenates and no significant increase in activity was observed following carrageenan treatment (FIG. 7).

EXAMPLE 7

Ex Vivo Inhibition of $cPLA_2$ and $iPLA_2$ Activity in Macrophages $cPLA_2$ and $iPLA_2$ are expressed in macrophage cells. It was therefore of interest to determine if the $PLA_2$ inhibitors of the invention acted on either or both of $cPLA_2$ and $iPLA_2$ in macrophages. To that end, $P388D_1$ murine macrophages were maintained at 37° C. in a humidified 10% $CO_2$ atmosphere. Cells were grown in Iscove's Modified Dulbecco's Medium (IMDM with 10% fetal calf serum (HyClone Labs, Provo Utah), 100 units/mL penicillin and 100 µg/mL streptomycin (Invitrogen, Carlsbad Calif.). Cells were routinely passaged every 2-3 days when the cells reached 75-80% confluence. Cells used for stimulation were plated at a density of $10^6$ cells per well in standard 12 well tissue culture plates and were allowed to adhere overnight.

Macrophages were stimulated by treating $P338D_1$ cells with either lipopolysaccharide (LPS) alone or LPS combined with platelet activating factor (PAF). Briefly, cells were washed twice with starvation media (IMDM containing 0.2% fetal calf serum, 100 units/mL penicillin and 100 µg/mL streptomycin) and then incubated with 1 mL of starvation media for one hour. Cells were then exposed to either 100 ng/mL LPS for 18 hours or 200 ng/mL LPS for one hour. Cells treated with 200 ng/mL LPS were then exposed to 100 nM PAF for 15 minutes. At the end of the stimulation, the media was removed from the cells, cleared of cellular debris by centrifugation and analyzed for prostaglandin $E_2$ ($PGE_2$) levels by enzyme-linked immunoassay (Cayman Chemical, Ann Arbor Mich.).

Inhibitor compounds were dissolved in DMSO and diluted into starvation media prior to addition to cells; the DMSO concentration was kept below 0.5% v/v in all studies. All inhibitors were added 30 minutes prior to stimulation.

Figure 14:
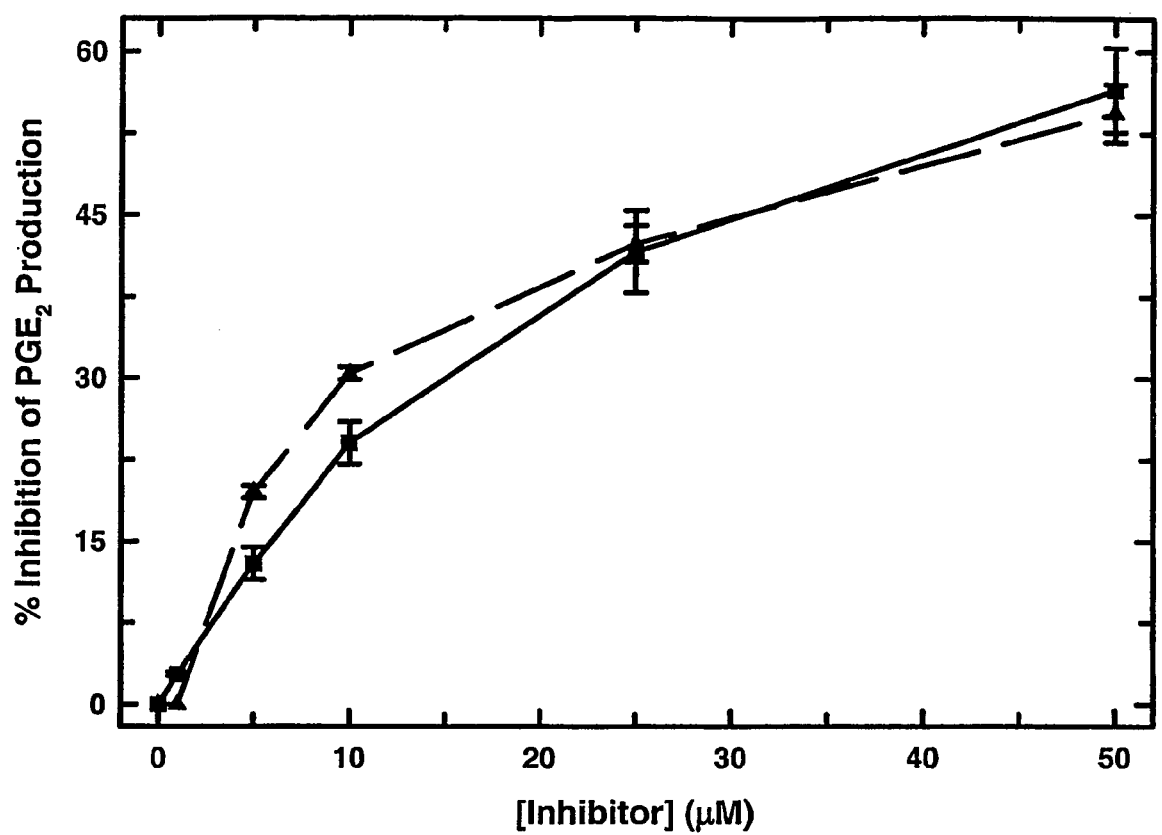
FIG. 14. Varying concentrations of OA1 (▲) or OA4 (■) were added to P388D$_1$ cells 30 min. prior to stimulation. The cells were then stimulated with LPS for 1 hour and PAF for 15 min as described. After stimulation, the media was harvested and the PGE$_2$ levels in the media were quantitated as described. The data were normalized to control DMSO-treated LPS/PAF-stimulated cells to appear as % inhibition. The data points are connected by a dashed line (OA1) and a solid line (OA4) for ease of visualization.

Both OA1 and OA4 were tested in the LPS/PAF-stimulation conditions (FIG. 14). Both of these inhibitors showed essentially identical inhibition of the $PGE_2$ release from the cells. The inhibition reached close to 60% at the maximal dosage tested (50 µM). Thus, the data shown in FIG. 14 indicate that compounds OA1 and OA4 inhibit $P388D_1$ $cPLA_2$ under the LPS/PAF stimulation conditions, resulting in the partial abrogation of $PGE_2$ release.

Figure 15:
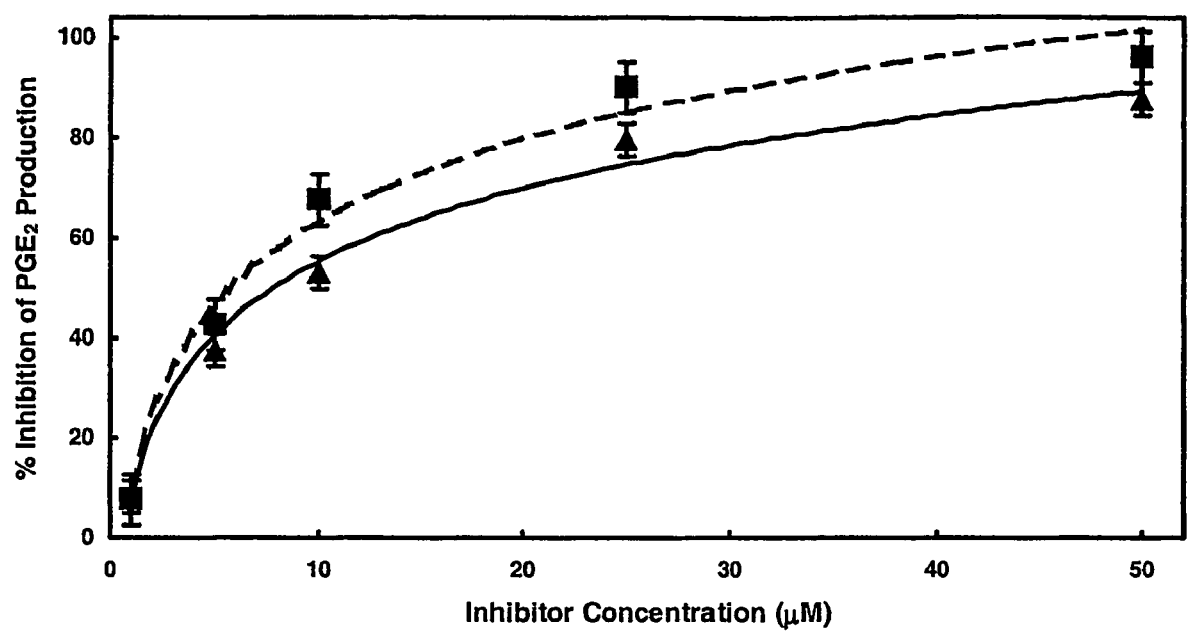
FIG. 15. Varying concentrations of OA1 (▲) or OA4 (■) were added to P388D$_1$ cells 30 min. prior to stimulation. The cells were then stimulated with LPS 18 hr as described. After stimulation, the media was harvested and the PGE$_2$ levels in the media were quantitated as described. The data were normalized to control DMSO-treated LPS-stimulated cells to appear as % inhibition. The lines correspond to a non-linear least squares fit of the data to logarithmic functions (OA1, solid curve and OA4, dashed curve). These functions were then used to calculate the IC$_{50}$ for OA1 (7.8 µM) and OA4 (5.8 µM).

Compounds OA1 and OA4 were also tested on the long-term LPS simulation conditions. As shown in FIG. 15, OA1 and were both able to completely block $PGE_2$ release with the addition of 50 µM inhibitor. Moreover, the data nicely fit to logarithmic functions and the $IC_{50}$ for the two inhibitors derived from these fits were 7.8 µM for OA1 and 5.8 µM for OA4.

EXAMPLE 8

Application of Synthesis Scheme to Production of Inhibitory Compound OA4

As a representative example of how the synthesis schemes for the inhibitory compounds of the invention may be applied, compound OA4 was synthesized as follows:

Benzyl(E,4S)-4-[(tert-butoxycarbonyl)amino]oct-2-enoate.

To a solution of 2-(tert-butoxycarbonylamino)hexanol (0.22 g, 1.0 mmol), in a mixture of EtOAc/toluene 1:1 (6 mL), a solution of NaBr (0.12 g, 1.1 mmol) in water (0.5 mL) and subsequently AcNH-TEMPO (2 mg, 0.01 mmol) were added at −10° C. To the resulting biphasic system was added under vigorous stirring a solution of NaOCl (0.08 g, 1.1 mmol) and $NaHCO_3$ (0.08 g, 1.0 mmol) in $H_2O$ (0.7 mL) dropwise at −10° C. over a period of 15 min. After stirring at −10° C. for 10 min EtOAc (15 mL) and water (5 mL) were added. The organic layer was washed with 1% aqueous citric acid (10 mL), which contained KI (0.5 g), 10% aqueous $Na_2S_2O_3$ (10 mL), brine and dried over $Na_2SO_4$. The solvent was evaporated under reduced pressure and the aldehyde was used directly to the next step without any purification.

To a solution of the aldehyde (0.21 g, 1.0 mmol) in dry THF (5 mL), $Ph_3P$=CHCOOBn (0.45 g, 1.1 mmol) was added and the reaction mixture was refluxed for 1 h. The solvent was evaporated under reduced pressure and the residue was purified by column chromatography (petroleum ether 40-60° C./EtOAc 9/1).

Yield 0.22 g (65%); $[\alpha]_D$ −9.6 (c 1 $CHCl_3$); MS (FAB): m/z (%): 348 (5) $[M+H^+]$; $^1H$ NMR: 7.36 (5H, m, $C_6H_5$), 6.90 (1H, dd, J=15.8 Hz, J=5.4 Hz, CH=CHCOO), 5.96 (1H, dd, J=15.8 Hz, J=1.4 Hz, CH=CHCOO), 5.18 (2H, s, $CH_2C_6H_5$), 4.51 (1H, d, J=7.8 Hz, NH), 4.28 (1H, m, CHNH), 1.62-1.17 (15H, m, 3×$CH_2$, C($CH_3)_3$), 0.90 (3H, t, J=6.0 Hz, $CH_3$); $^{13}C$ NMR: 166.4, 155.4, 149.6, 128.7, 128.5, 136.1, 120.4, 79.9, 66.5, 51.7, 34.6, 28.0, 22.6, 28.6, 14.1; Anal. Calcd. for $C_{20}H_{29}NO_4$: C, 69.14; H, 8.41; N, 4.03. Found: C, 69.05; H, 8.68; N, 3.84.

(E,4S)-1-(Benzyloxy)-1-oxooct-2-en-4-aminium chloride.

Benzyl(E,4S)-4-[(tert-butoxycarbonyl)amino]oct-2-enoate (0.35 g, 1.0 mmol) was treated with 4 N HCl in $Et_2O$ (8 mL) for 1 h at room temperature. The solvent and the excess acid were evaporated under reduced pressure and the residue was reevaporated twice from $Et_2O$.

Yield 0.24 g (84%); $[\alpha]_D$ 10.8 (c 0.5 MeOH); mp 108-110° C.; $^1$H NMR δ 7.35 (5H, m, $C_6H_5$), 6.92 (1H, dd, J=15.6 Hz, J=7.0 Hz, CH=CHCOO), 6.19 (1H, d, J=15.6 Hz, CH=CHCOO), 5.17 (2H, s, $CH_2C_6H_5$), 3.91 (1H, m, $CHNH_3^+$), 1.85 (2H, m, $CH_2CHNH_3^+$), 1.32 (4H, s, 2×$CH_2$), 0.88 (3H, t, J=6.0 Hz, $CH_3$); $^{13}$C NMR δ 165.1, 141.9, 128.6, 128.3, 135.4, 125.0, 66.5 ($CH_2C_6H_5$), 52.6, 32.5, 27.2, 22.0, 13.7.

Benzyl(E,4S)-4-[(2-hydroxydodecanoyl)amino]oct-2-enoate.

To a stirred solution of 2-hydroxyhexadecanoic acid (0.54 g, 2.0 mmol) and (E,4S)-1-(benzyloxy)-1-oxooct-2-en-4-aminium chloride (0.28 g, 1.0 mmol) in $CH_2Cl_2$ (5 mL), $Et_3N$ (0.3 mL) and subsequently WSCI (0.57 g, 3.0 mmol) and HOBt (0.32 g, 2.0 mmol) were added at 0° C. The reaction mixture was stirred for 1 h at 0° C. and at room temperature for 1 day. The organic layer was washed with brine, dried over $Na_2SO_4$ and evaporated under reduced pressure. The residue was purified by column chromatography ($CHCl_3$/MeOH 98/2). Yield 0.33 g (75%); $[\alpha]_D$−10.3 (c 0.5 $CHCl_3$);

MS (FAB): m/z (%): 446 (45) [M+H$^+$]; $^1$H NMR δ7.35 (5H, m, $C_6H_5$), 6.90 (1H, dd, J=15.6 Hz, J=5.4 Hz, CH=CHCOO), 6.65 (1H, m, NH), 5.92 (1H, dd, J=15.6 Hz, J=1.8 Hz, CH=CHCOO), 5.16 (2H, s, $CH_2C_6H_5$), 4.62 (1H, m, CHNH), 4.13 (1H, m, CHOH), 1.90-1.11 (24H, m, 12×$CH_2$), 0.88 (3H, t, J=6.0 Hz, $CH_3$); $^{13}$C NMR: 173.4, 166.0, 148.4, 128.6, 128.3, 135.7, 120.5, 72.2, 66.4, 49.5, 34.9, 34.7, 33.9, 31.9, 29.5, 29.3, 27.7, 25.0, 24.9, 22.6, 22.4, 22.3, 14.1, 13.8.

(4S)-4-[(2-Hydroxydodecanoyl)amino]octanoic acid.

To a solution of benzyl (E,4S)-4-[(2-hydroxydodecanoyl) amino]oct-2-enoate (0.445 g, 1 mmol) in EtOH (2.5 mL), through which $N_2$ had been passed for 5 min, 10% Pd/C catalyst (0.042 g) was added. The reaction mixture was stirred under $H_2$ for 5 h at room temperature. The catalyst was removed by filtration through a pad of Celite and the filtrate was evaporated under reduced pressure. The product was purified by column chromatography ($CHCl_3$/MeOH 9/1). Yield 0.28 g (70%); mp 53-55° C.; $[\alpha]_D$−2.4 (c 0.75 $CHCl_3$); $^1$H NMR δ 6.82 (1H, m, NH), 4.18 (1H, m, CHNH), 3.91 (1H, m, CHOH), 2.39 (2H, t, J=6.3 Hz, $CH_2COOH$), 1.95-1.12 (26H, m, 13×$CH_2$), 0.88 (3H, t, J=6.0 Hz, $CH_3$); Anal. Calcd. for $C_{20}H_{39}NO_4$: C, 67.19; H, 10.99; N, 3.92. Found: C, 67.05; H, 11.18; N, 3.63.

(4S)-4-[(2-Oxododecanoyl)amino]octanoic acid (OA4).

To a solution of (4S)-4-[(2-hydroxydodecanoyl)amino]octanoic acid (0.36 g, 1.0 mmol) in glacial acetic acid (4 mL), PDC (1.13 g, 3.0 mmol) was added. After stirring for 2 h at room temperature, the mixture was neutralized with 5% aqueous $NaHCO_3$ and extracted with EtOAc (20 mL×3). The combined organic layers were washed with brine solution and dried ($Na_2SO_4$). The solvent was evaporated under reduced pressure and the crude product was purified by column chromatography (petroleum ether 40-60° C./EtOAc 5/5).

Yield 0.20 g (57%); mp 50-52° C.; $[\alpha]_D$−1.8 (c 0.5 $CHCl_3$); MS (FAB): m/z (%): 378 (35) [M+Na$^+$], 356 (45) [M+H$^+$]; $^1$H NMR δ 6.86 (1H, d, J=9.4 Hz, NH), 3.90 (1H, m, CHNH), 2.90 (2H, t, J=7.8 Hz, $CH_2COCO$), 2.35 (2H, t, J=6.3 Hz, $CH_2COOH$), 2.01-1.05 (24H, m, 12×$CH_2$), 0.87 (3H, t, J=6.0 Hz, $CH_3$); $^{13}$C NMR: 199.4, 178.5, 160.1, 49.3, 36.8, 34.7, 31.8, 30.7, 29.8, 29.5, 29.4, 29.3, 29.2, 29.0, 27.9, 23.1, 22.6, 22.4, 14.1, 13.9; Anal. Calcd. for $C_{20}H_{37}NO_4$: C, 67.57; H, 10.49; N, 3.94. Found: C, 67.35; H, 10.77; N, 3.98.

Other embodiments are within the following claims. In addition, where features or aspects of the invention are described in terms of Markush groups, those skilled in the art will recognize that the invention is also thereby described in terms of any individual member or subgroup of members of the Markush group.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

What is claimed is:
1. A compound of the formula (I):

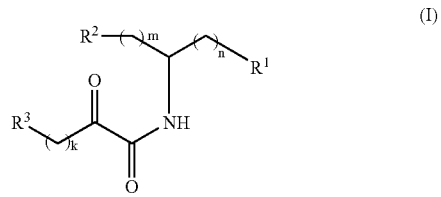

wherein:
R$^1$ is an acidic moiety, selected from the group consisting of carboxyl, phosphate, phosphinate, sulfate, and sulfonate; each of R$^2$ and R$^3$ is a moiety independently selected from the group consisting of phenyl, benzyl, and a carbyl having between 1 and 13 carbons, the carbyl being selected from the group consisting of a linear or branched, saturated or unsaturated alkyl, alkenyl, and alkynyl;

n is an integer having a value of 3, m is an integer having a value of 0 to 3, and k is an integer having a value of 0 to 22;

and isomers, enantiomers, and pharmacologically or immunologically acceptable salts thereof.

2. A pharmaceutical composition, comprising (4S)-4-[(2-oxododecanoyl)amino]octanoic acid, and a pharmaceutically acceptable carrier.

3. A pharmaceutical composition, comprising 4-[(2-oxohexadecanoyl)amino]butanoic acid, and a pharmaceutically acceptable carrier.

4. A pharmaceutical composition, comprising 4-[(2-oxooctanoyl)amino]butanoic acid, and a pharmaceutically acceptable carrier.

5. A pharmaceutical composition, comprising (4R)-4-[(2-oxododecanoyl)amino]octanoic acid, and a pharmaceutically acceptable carrier.

6. A pharmaceutical composition, comprising the compound of formula (II),

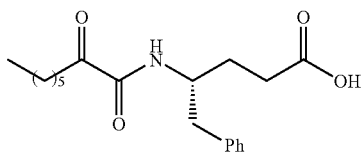
(II)

and a pharmaceutically acceptable carrier.

7. A pharmaceutical composition, comprising the compound of formula (III),

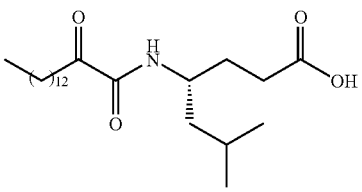
(III)

and a pharmaceutically acceptable carrier.

8. A pharmaceutical composition, comprising the compound of formula (IV),

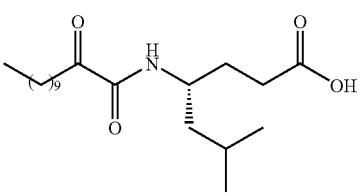
(IV)

and a pharmaceutically acceptable carrier.

9. A pharmaceutical composition, comprising the compound of formula (V),

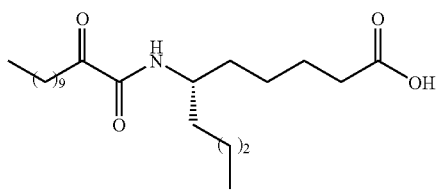
(V)

and a pharmaceutically acceptable carrier.

10. A pharmaceutical composition, comprising the compound of formula (VI),

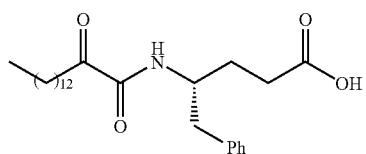
(VI)

and a pharmaceutically acceptable carrier.

11. A pharmaceutical composition, comprising the compound of formula (VII),

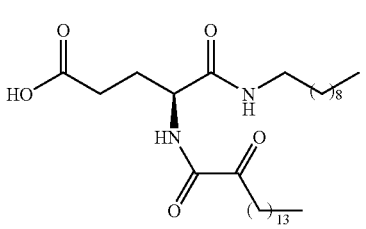
(VII)

and a pharmaceutically acceptable carrier.

12. A pharmaceutical composition, comprising the compound of formula (VIII),

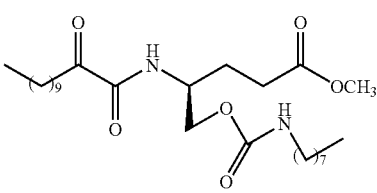
(VIII)

and a pharmaceutically acceptable carrier.

* * * * *